(12) United States Patent
Davis et al.

(10) Patent No.: US 9,164,115 B2
(45) Date of Patent: Oct. 20, 2015

(54) HIGH-SPEED, AUTOMATED CHROMATOGRAPHIC ANALYZER FOR DETERMINATION OF NONGLYCATED AND GLYCATED PROTEINACEOUS SPECIES IN BLOOD SAMPLES

(75) Inventors: Jon Davis, Kansas City, MO (US); Roger L. Donley, Overland Park, KS (US); Michael Farnet, Lenexa, KS (US); Harold M. Donley, Pleasant Hill, MO (US); Seth Powers, Kansas City, MO (US); Joshua Wears, Kansas City, MO (US); Sam Schlageck, Kansas City, MO (US)

(73) Assignee: Trinity Biotech, primus Corporation, Kansas, KS (US)

( * ) Notice: Subject to any disclaimer, the term of this patent is extended or adjusted under 35 U.S.C. 154(b) by 354 days.

(21) Appl. No.: 13/422,630

(22) Filed: Mar. 16, 2012

(65) Prior Publication Data
US 2013/0243654 A1    Sep. 19, 2013

(51) Int. Cl.
G01N 35/04    (2006.01)
G01N 30/88    (2006.01)
G01N 35/10    (2006.01)
G01N 35/02    (2006.01)

(52) U.S. Cl.
CPC .............. *G01N 35/04* (2013.01); *G01N 35/025* (2013.01); *G01N 35/026* (2013.01); *G01N 2030/8813* (2013.01); *G01N 2035/0498* (2013.01); *G01N 2035/1032* (2013.01)

(58) Field of Classification Search
CPC ..... G01N 1/02; G01N 1/10; G01N 35/00584; G01N 35/026; G01N 35/04; G01N 2035/046; Y10T 436/113332; Y01T 436/114165; Y01T 436/114998
USPC ......................................... 422/63, 65; 436/47
See application file for complete search history.

(56) References Cited

U.S. PATENT DOCUMENTS

| | | | | |
|---|---|---|---|---|
| 4,966,853 | A * | 10/1990 | Matsuda et al. | 435/289.1 |
| 5,232,665 | A * | 8/1993 | Burkovich et al. | 422/65 |
| 6,020,203 | A | 2/2000 | Rexroad, Jr. et al. | |
| 6,534,307 | B1 * | 3/2003 | Muraca | 506/40 |
| 6,958,130 | B1 * | 10/2005 | Gicquel et al. | 422/65 |
| 2002/0064886 | A1 * | 5/2002 | Nakagawa et al. | 436/177 |
| 2005/0037485 | A1 * | 2/2005 | Rodgers et al. | 435/287.2 |

* cited by examiner

*Primary Examiner* — Jan Ludlow
(74) *Attorney, Agent, or Firm* — Hovey Williams LLP

(57) ABSTRACT

High-speed, automated analyzers for analyzes of biological fluids, such as whole blood or blood-derived components, include specialized analyzer and sample transfer features permitting injection-to-injection analysis times on the order of one minute. The analyzers are particularly designed for HPLC analysis for glycated and nonglycated proteinaceous species in blood samples.

23 Claims, 17 Drawing Sheets

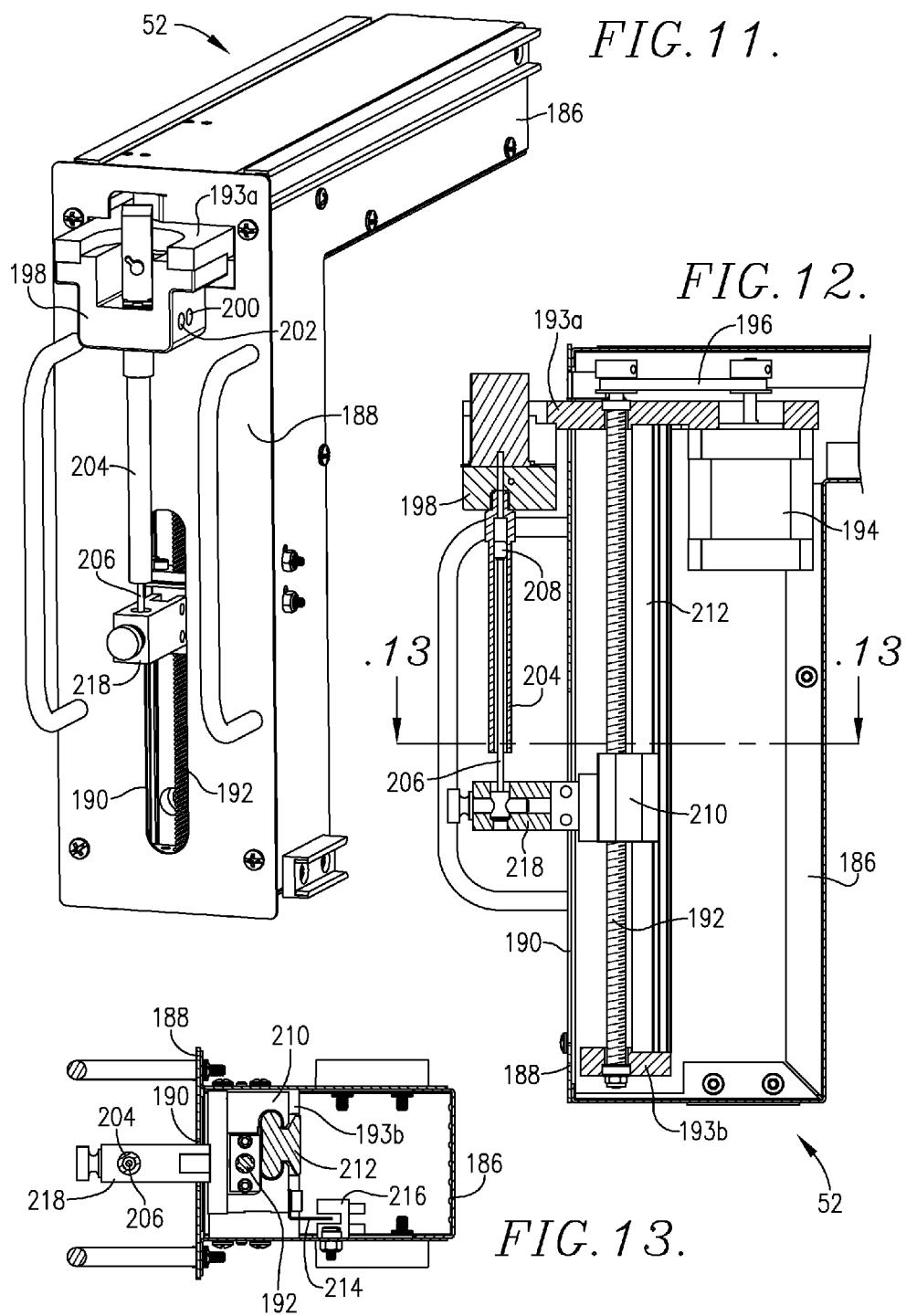

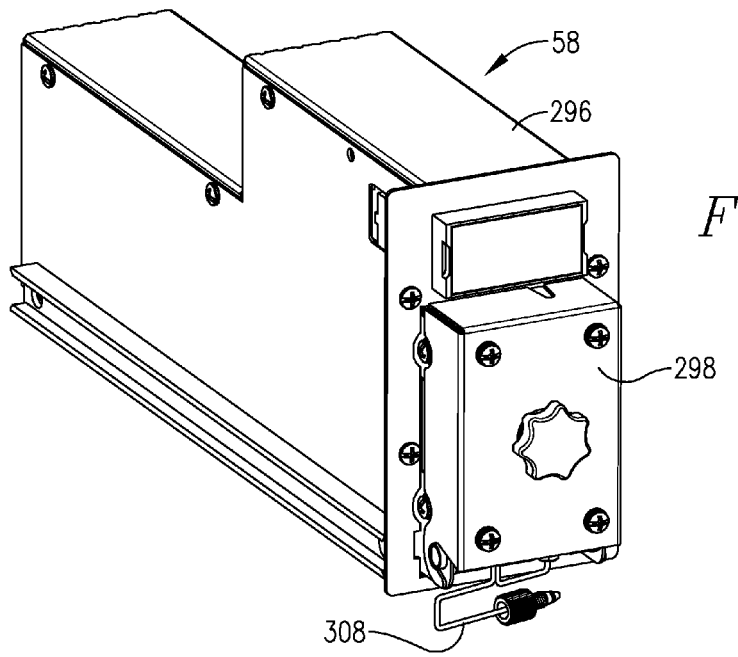
FIG. 22.
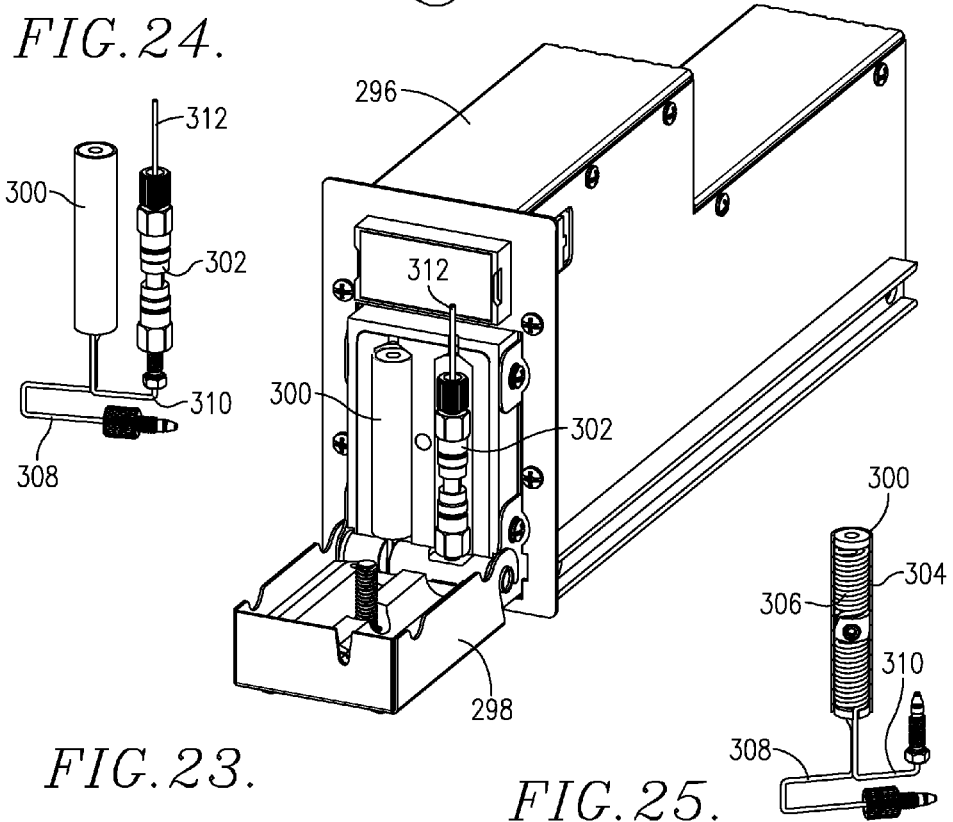
FIG. 24.
FIG. 23.
FIG. 25.

HIGH-SPEED, AUTOMATED CHROMATOGRAPHIC ANALYZER FOR DETERMINATION OF NONGLYCATED AND GLYCATED PROTEINACEOUS SPECIES IN BLOOD SAMPLES

BACKGROUND OF THE INVENTION

1. Field of the Invention

The present invention is broadly concerned with automated chromatographic analyzer apparatus which can be used to analyze a variety of biological samples, such as whole blood and blood-derived components. More particularly, the invention is concerned with such apparatus which is especially designed for high-speed, accurate analyses of blood samples in order to quantitatively determine glycated and nonglycated proteinaceous fractions therein. Such analyses are valuable to determine diabetes conditions in patients.

2. Description of the Prior Art

The measurement of glycated protein in the blood of a patient suffering from diabetes mellitus provides an attending physician with a means for assessing blood sugar control over different periods of time. As a consequence, considerable research has been done in the past to develop accurate, rapid analyses for glycated proteins. In order to be truly effective, however, such methods should also be capable of measuring the glycated protein content of both hemoglobin and plasma (serum) proteins. This stems from the fact that the percentage of glycated hemoglobin in a sample is a measure of mean blood sugar concentrations for the preceding 45 to 60 days, whereas the percentage of glycated plasma protein reflects blood sugar concentrations over a shorter period, approximately 1-3 weeks prior to analysis.

It is known that non-enzymatically glycated proteins such as hemoglobins and circulating plasma or serum proteins differ from nonglycated species by the attachment of sugar moieties to the proteins at various binding sites by means of a ketoamine bond. Glycated proteins thus contain functional groups (sometimes reported as 1,2-cis-diol groups) not found in nonglycated proteins. The presence of such functional groups thus provides a basis for separation of glycated and nonglycated proteins.

One prior technique for separating glycated and nonglycated protein fractions is known as boronate affinity chromatography. This analysis relies on the fact that borates or boronates, such as m-aminophenylboronic acid (PBA), can under certain conditions, bond with the functional groups in glycated proteins. The bonds in the resulting complex are reversible in aqueous solution. In the typical chromatographic system, the boronate is immobilized on a support medium in a chromatographic column. A solution containing the substance under analysis, such as hemoglobin or plasma (serum), is applied to the column, wherein the glycated components bond with the boronate. Nonglycated components are washed out of the column with a suitable buffer solution, then eluated from the column and collected separately. Eluation of the glycated components is achieved by means of either: 1) a buffer solution containing a competing polyol, which replaces the protein in the boronate complex, or 2) a buffer or acid solution of low (below neutrality) pH.

A number of secondary factors, such as interactions between boronates and amines or carboxyls, influence the chromatographic separation. Complex molecules such as proteins also engage in hydrophobic, ionic, hydrogen-bond, and charge-transfer interactions. The need to design chromatographic systems which maximize the specific binding of boronates with diol-containing glycated proteins is therefore complicated by the need to also minimize the binding of nonglycated proteins through nonspecific interactions. Many factors such as buffer composition, molarity, ion content, ligand concentration and pH are known to influence the boronate affinity chromatographic separation of glycated and nonglycated proteins.

Glycated and nonglycated proteins separated chromatographically are commonly quantitated spectrophotometrically. For hemoglobin quantitation, the spectrophotometer is set to measure the absorbance of light in or near the "Soret region" (413-415 nanometers), which is the range of peak absorbance for hemoglobin. For plasma (serum) protein quantitation, the spectrophotometer is set to measure the absorbance of light in the 280 nanometer range, at which the proteins show peak absorbance. Of course, other wavelength determinations can also be maintained using known chromagens in the eluates. The buffer solution used to elute the non-glycated components is first placed in the light path of the spectrophotometer. The spectrophotometer is then adjusted so that zero absorbance is displayed on the scale or readout. This procedure, called a "blank", corrects for the background absorbance of the contents of the buffer solution. The next step is to place the non-glycated protein-containing buffer solution in the light path of the spectrophotometer and record the absorbance of light. By virtue of the "blanking" procedure, any increase in the absorbance of light by the protein-containing solution is due entirely to the protein content.

The same procedure is used for the eluate containing the glycated components; that is, the spectrophotometer is first "blanked" with the elution buffer solution in the light path, after which the increase in absorbance of the protein-containing buffer is recorded. Quantitation is then achieved by calculation. The increase in absorbance over the "blank" solutions of the protein-containing solutions is directly proportional to the protein content. The calculation also takes into account the dilution of the proteins by the buffer solutions. The result of this calculation is the expression of the glycated components as a percentage of the whole, e.g., "10% glycated hemoglobin" or "14% glycated plasma proteins."

The above procedure, although somewhat effective in yielding accurate hemoglobin protein analyses, is generally inaccurate or imprecise in serum protein analyses, and moreover is less suited for commercial laboratories because the protocol is very time consuming and costly. Thus, the need to individually collect and subsequently blank each of the eluates presents a significant drawback in the context of multiple analyses in a large laboratory.

U.S. Pat. No. 6,020,203 describes significant improvement in the art and is capable of short sample injection-to-injection times on the order of 8 minutes. In this technique, use is made of "spectrophotometrically balanced" reagents to transfer the sample through the PBA column and spectrophotometer, and to regenerate the column after each sample separation. However, the preferred apparatus described in the '203 patent is rather large and cumbersome, and has a significant footprint. Moreover, the equipment is not modularized for optimal operation and servicing.

SUMMARY OF THE INVENTION

The present invention overcomes the problems outlined above and provides a greatly improved analyzers having a number of features which provide high-speed, continuous analyses of biological samples, such as blood, blood components, or other body fluids, extracts, or emulsions. A particular utility of the invention is provision of HPLC analyzers for quantitatively and/or qualitatively determining glycated and nonglycated protein fractions within samples. The preferred analyzers are of modular design, including respective modules which may be individually removed for service or replacement.

Generally speaking, the analyzers of the invention are operable to handle individual racks of sample tubes where each tube contains a respective biological fluid sample, a pierceable septum, and an external, uniquely identifying bar code. The analyzers serially analyze each sample during the handling of the racks. To this end, the analyzers of the invention include a shiftable needle operable to pierce the septum of each sample tube and to take a sample aliquot from each tube, and to inject the aliquots for downstream analysis thereof, typically by column separation and spectrophotometric analysis. As such, it is important that the racks and sample tubes be identified and optimally handled during the course of sample analysis.

Accordingly, the analyzers of the invention include structure operably supporting the analysis needle in order to selectively axially rotate the needle, and to selectively axially shift the needle. The preferred needle-supporting structure comprises a needle body presenting a non-round surface portion (preferably a pair of opposed, flattened surfaces), and a rotatable spindle receiving the non-round surface portion, with the needle support being axially rotatable in response to rotation of the spindle. This overall structure further includes apparatus operably coupled with the needle support for selective vertical shifting movement of the needle support and the needle. In this fashion, when the needle pierces the septum of each sample, the frictional engagement between the needle and the septum causes rotation of the sample tube in response to rotation of the needle. This tube rotation continues until the analyzer bar code reader detects the external identifying bar code on the sample tube. At the same time, the vertical reciprocation of the needle is maintained.

In addition, a specialized apparatus is provided for selective shifting of the racks containing the sample tubes. This apparatus includes a generally quadrate, elongated base plate presenting a pair of opposed side margins and a pair of opposed end margins. A fore-and-aft shifting assembly is also provided which is operable to individually shift each of the racks in a first direction adjacent one of the side margins, and in the opposite direction along the other of the side margins, along with a lateral shifting mechanism operable to shift each of the racks in a first lateral direction adjacent one of the end margins, and in the opposite lateral direction adjacent the other of the end margins. Accordingly, each of the racks follows a quadrate path of travel around the base plate. After all of the samples in all of the racks have been analyzed, fresh racks are installed in the analyzer, and the analysis process is repeated.

Preferably, the fore-and-aft shifting assembly including a pair of elongated, shiftable belts respectively located adjacent and outboard of the side margins of the base plate and shiftable in opposite directions, respectively, each of the belts supporting a rack shifter operable to engage and axially shift a respective rack. The lateral shifting mechanism comprises a first pair of axially spaced apart, laterally extending rack-supporting belts proximal to one of the base plate end margins, and a second pair of axially spaced apart, laterally extending rack-supporting belts proximal to the other of the base plate end margins, the first pair of belts shiftable in one direction, and the other pair of belts shiftable in the opposite direction.

In particularly preferred forms, the belts of the first and second belt pairs are each supported on a pair of eccentric pulleys, the pulleys operable to withdraw end sections of the belts below the base plate in order to prevent interference between the belts and the fore-and-aft shifting of the racks along the base plate. Additionally, one pulley of each of the sets thereof includes a rack-engaging lug operable during rotation of the pulley to engage an adjacent rack to assist in lateral movement thereof.

BRIEF DESCRIPTION OF THE DRAWINGS

FIG. 11 is a perspective view of the syringe module;

FIG. 12 is a vertical view of the syringe module;

FIG. 13 is a horizontal sectional view taken along line 13-13 of FIG. 12;

FIG. 22 is a perspective view of the oven module;

FIG. 23 is a perspective view of the oven module, with the door thereof open to reveal the HPLC column and oven coil;

FIG. 24 illustrates the interconnection between the oven coil and column;

FIG. 25 is a partial sectional view of the oven coil;

FIG. 27 is a perspective view illustrating one of the sample racks loaded with tubes with bar codes for identification of the rack and the individual sample tubes therein.

DETAILED DESCRIPTION OF THE PREFERRED EMBODIMENT

Figure 1:
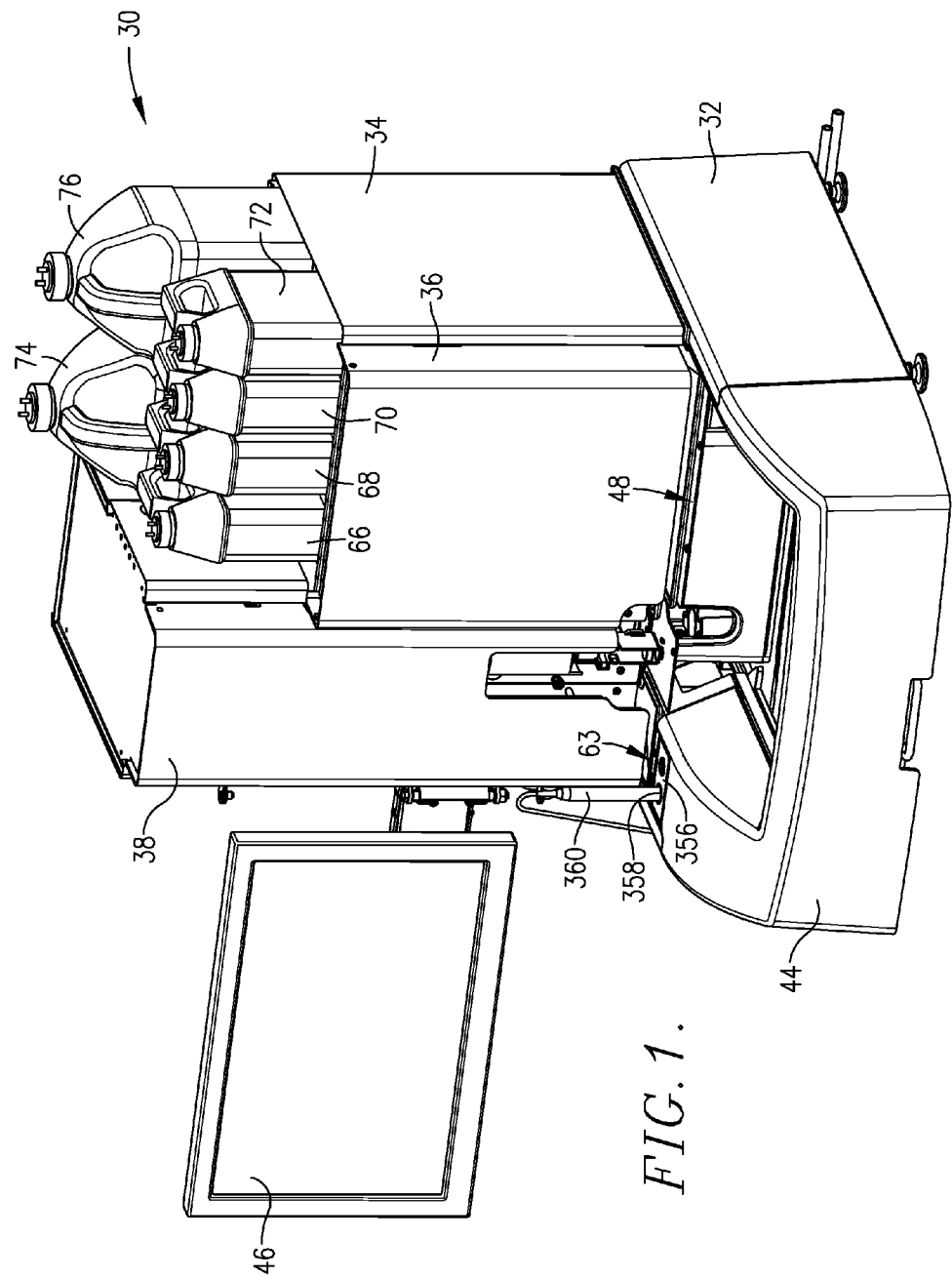
FIG. 1 is a perspective view of an analyzer in accordance with the invention.
Figure 2:
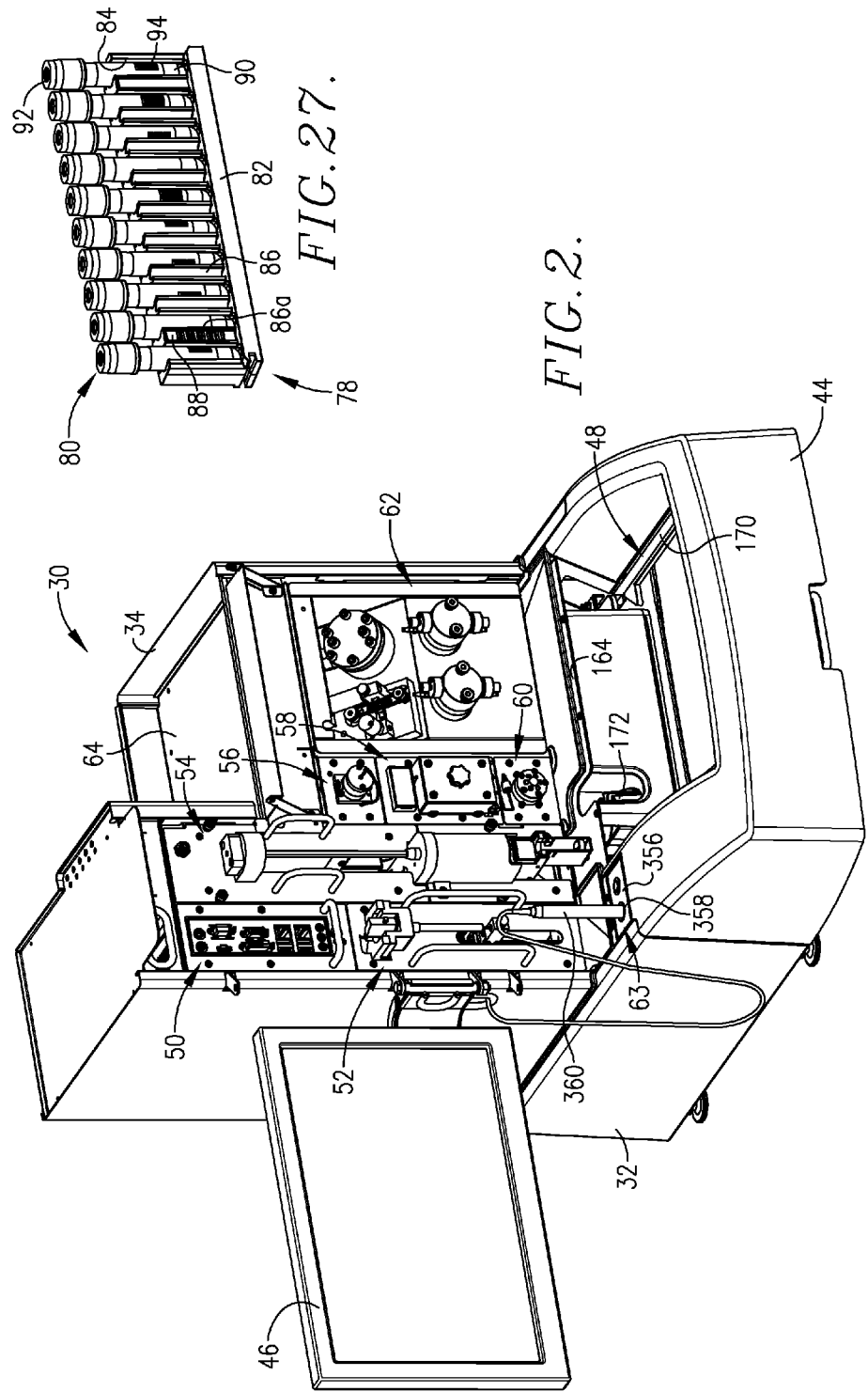
FIG. 2 is another perspective view of the analyzer, with protective covers removed to illustrate the modules of the analyzer.
Figure 3:
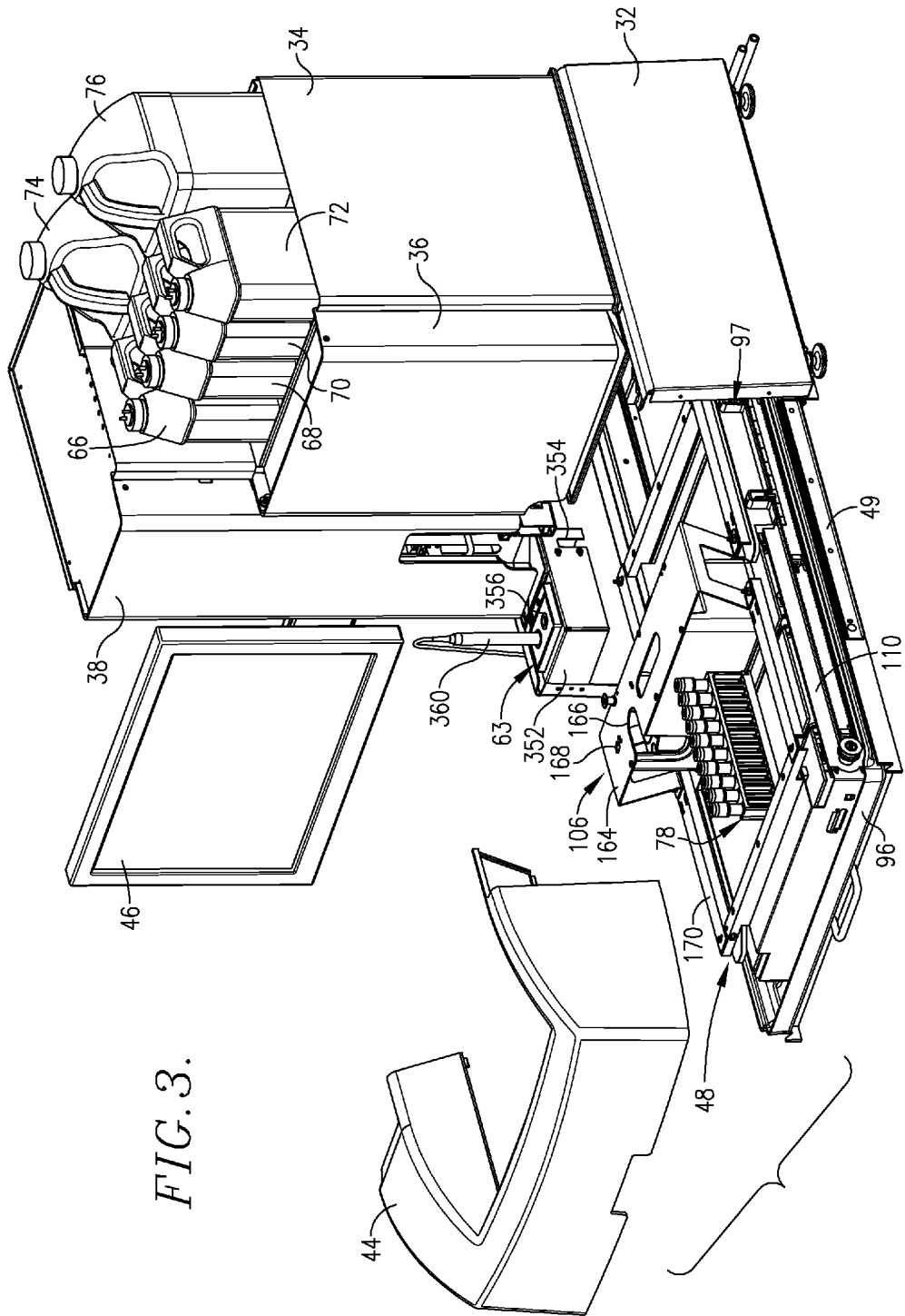
FIG. 3 is another perspective view of the analyzer, illustrated with the conveyor module extended for loading or service.

Turning now to the drawings, and particularly FIGS. 1, 2, 10, and 26, the analyzer 30 include covers 34, 36, and 38, and a detachable, forwardly extending, generally U-shaped cover 44. The apparatus further includes a monitor 46 and would also have an input keyboard (not shown). FIG. 2 illustrates the analyzer 30 with the covers 36-38 removed to depict the modules of the analyzer, namely the conveyor module 48, motherboard module 50, syringe module 52, probe module 54, detector module 56, oven module 58, injector module 60, and pump module 62. A bar code scanner assembly 63 is also provided forwardly of the syringe module 52 (FIGS. 1-3). The aforementioned chassis is equipped with guide rails and stops permitting easy removal and replacement of the modules, as may be necessary during the course of operation of the analyzer 30.

As best seen in FIG. 2, a liquids tray 64 is located above the modules 56 and 58 and supports a series of liquid bottles including (FIG. 1) bottle 66 containing cleaning reagent, bottle 68 containing reagent A, bottle 70 containing reagent B, bottle 72 containing water, and bottles 74 and 76 containing aqueous diluent.

A principal feature of the present invention is the provision of an analyzer which is fully modular, in that the respective modules 48-62 may be individually removed from the overall analyzer for service or replacement. This also creates an analyzer having a relatively small footprint, as compared with analyzers of the prior art.

The analyzer 30 is designed to receive a series of sample racks 78 (FIG. 27) each containing a number of identical sample tubes 80 therein, and to individually analyze the contents thereof. The rack 78 has a base plate 82 and a series of upstanding tube-receiving compartments 84 defined by upwardly extending, laterally spaced apart segments 86. One segment 86a carries a bar code 88 which uniquely identifies the respective rack. Each of the sample tubes 80 includes an elongated tube section 90 with an uppermost septum 92. Furthermore, each tube section 90 carries a bar code 94 which uniquely identifies the individual tube 80.

Conveyor Module 48

The conveyor module 48 is supported by tray 96 which is in turn supported by a drawer assembly 49. The module 48 has a rack-shifting assembly 97 including a frame assembly 98, a fore-and-aft rack transport mechanism 100, two lateral rack transport mechanisms 102 and 104, and a bridge assembly 106. The purpose of conveyor module 48 is to efficiently handle a plurality of racks 78 each carrying loaded sample tubes 80 so as to sequentially move each rack 78 into a test station adjacent bar code reader assembly 63, and to thereupon index the so-positioned rack, so that each tube 80 thereof is successively moved to a fixed test position beneath probe module 54. After all of the tubes 80 within the rack 78 are tested, the rack is then moved to a rearward storage location and a fresh rack is moved into the test station. After all of the sample tubes of all of the racks within the assembly 97 are analyzed, the in-place assembly 97 may be reloaded with new racks 78, or the assembly 97 may be bodily removed from tray 96 to allow installation of a fresh, loaded assembly 97.

Figure 4:
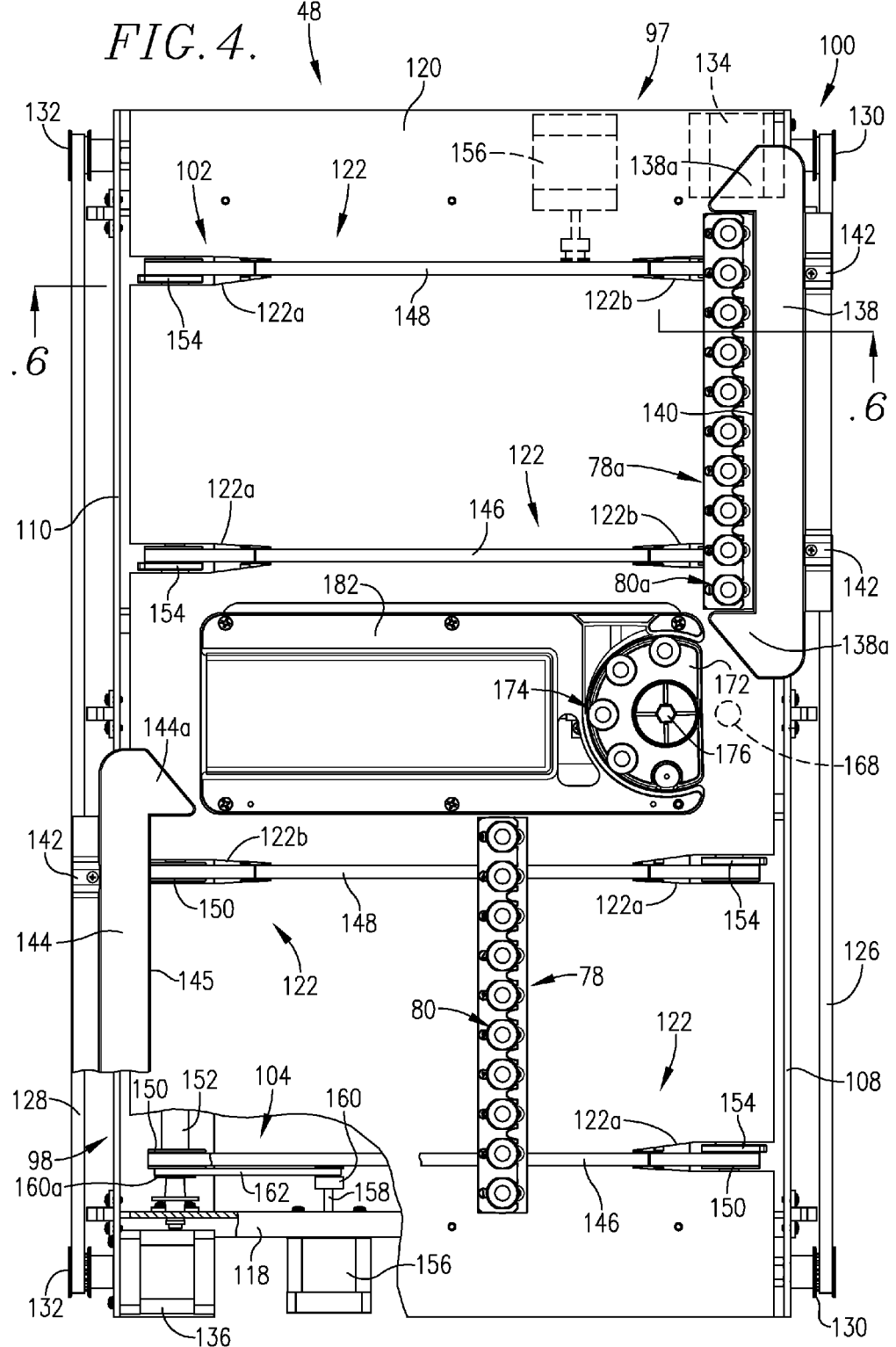
FIG. 4 is a plan view of the sample conveyor forming a part of the conveyor module, with the upper frame removed and parts broken away to illustrate details of construction.
Figure 5:
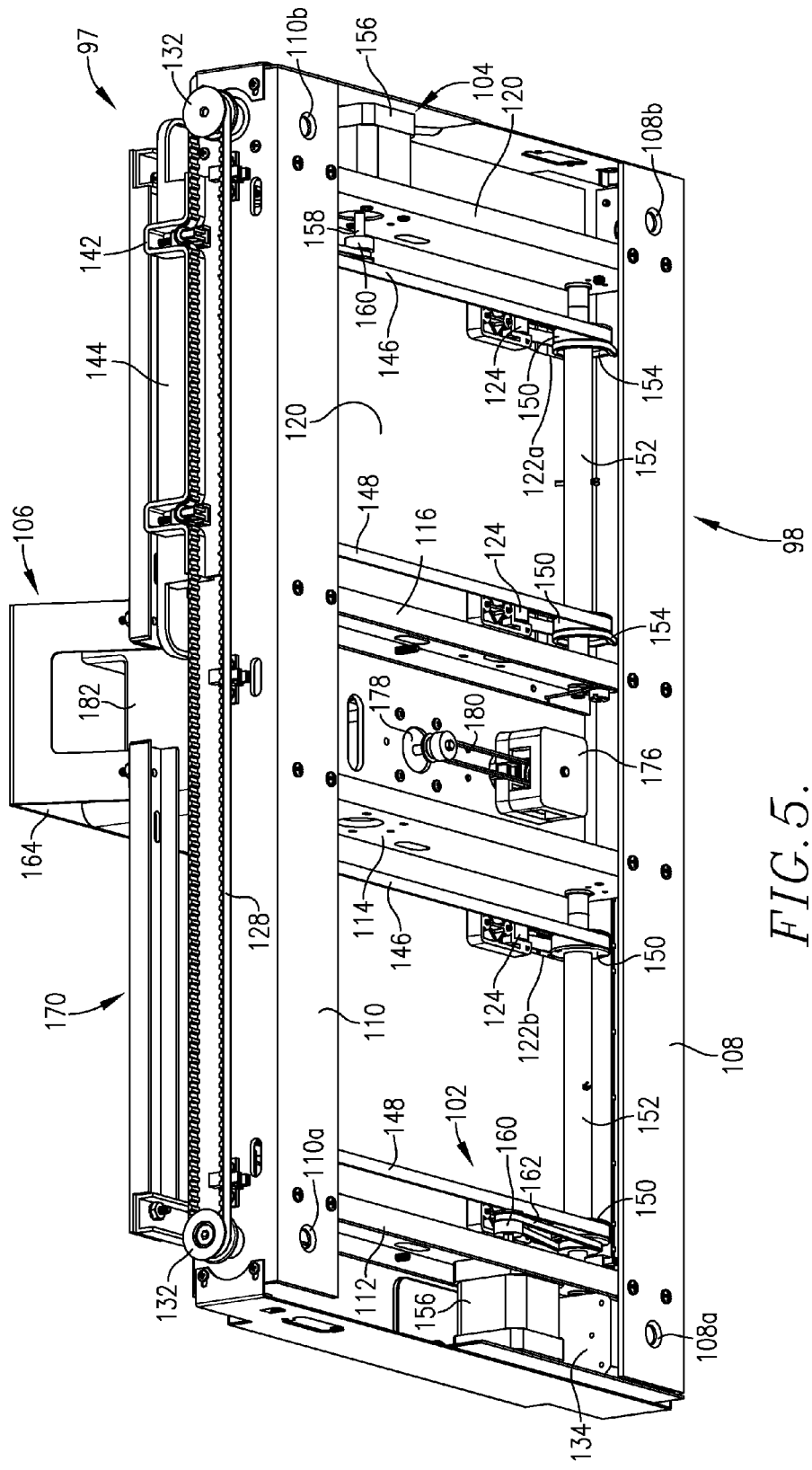
FIG. 5 is a bottom perspective view of the conveyor module, illustrating the fore-and-aft rack shifting drive and the lateral rack moving belts.

The frame assembly 98 includes two generally L-shaped, fore-and-aft extending side rails 108, 110 and spaced apart cross rails 112, 114, 116, and 118. The side rails 108, 110 (FIG. 5) have positioning apertures 108a, 108b and 110a, 110b adjacent the ends thereof (FIG. 5). The conveyor assembly 48 is mounted by means of four locating pins mounted on a drawer assembly 49 which extend though corresponding tubular tray-mounted grommets (not shown) and into the apertures 108a, 108b and 110a, 110b. The overall frame assembly 48 further has a slotted base plate 120 supported by the cross rails 112-118 between the side rails 108, 110. The base plate 120 includes two pairs of spaced apart lateral belt slots 122, each including a relatively wide slot 122a and an opposed, narrower slot 122b (FIG. 4). A series of belt rollers 124 are secured to the underside of base plate 120 closely adjacent the inner margin of each slot 122a, 122b. It will be observed that the base plate 120 is substantially quadrate in plan configuration, presenting a pair of opposed fore-and-aft extending side margins, and a pair of opposed end margins.

The transport mechanism 100 includes a pair of continuous belts 126, 128 respectively support on endmost rollers 130 and 132. The belt 126 is driven by motor 134, whereas belt 128 is driven by 136. An elongated rack shifter 138 having endmost, inwardly extending, rack-engaging ears 138a which cooperatively define a rack-receiving recess 140 is supported by the side rail and is attached to belt 130 by means of belt couplers 142 (FIG. 5); similarly, an identical rack shifter 144 having ears 144a defining a rack-receiving recess 145 is supported by side rail 110 to belt 128 via couplers 142.

Figure 6:
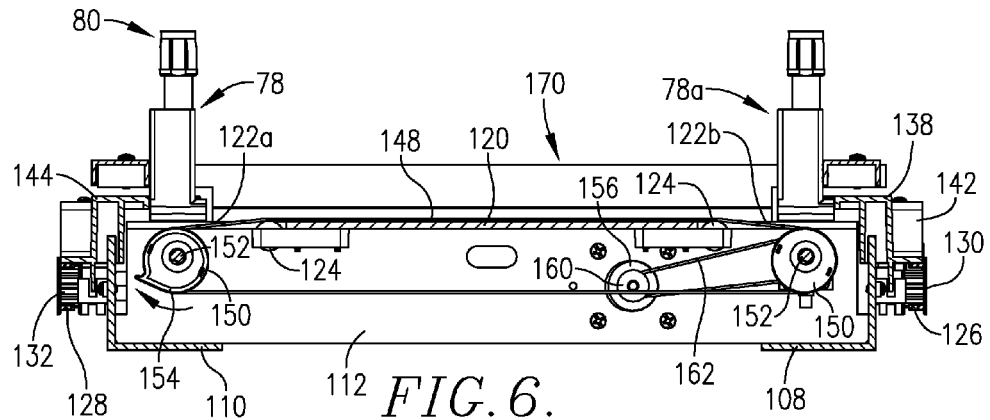
FIG. 6 is a vertical sectional view taken along line 6-6 of FIG. 4, and depicting the lateral rack moving belts with the eccentric belt pulleys shown in the belts-down position permitting movement of a sample rack in a fore-and-aft direction without belt interference.

The lateral rack transport mechanism 102 includes a pair of laterally extending continuous belts 146 and 148, each supported by a pair of endmost eccentric pulleys 150 secured to common cross shafts 152. As illustrated, the upper runs of each of the belts 146, 148 pass around the pulleys 150 and through the slots 122a, 122b to move along the upper surface of base plate 120. Moreover (FIG. 6), the pulleys 150 adjacent the slots 122a are equipped with rotary lug plates 154, which are important for purposes to be described. The belts 146, 148 are driven via a motor 156 member 112 having an output shaft 158 supporting a drive pulley 160. A drive belt 162 passes around pulley 160 and the small concentric pulley 160a adjacent the slot 122b. The lateral transport mechanism 104 is identical with the mechanism 102 and accordingly like reference numerals are used to identify the components thereof.

Figures 8, 9:
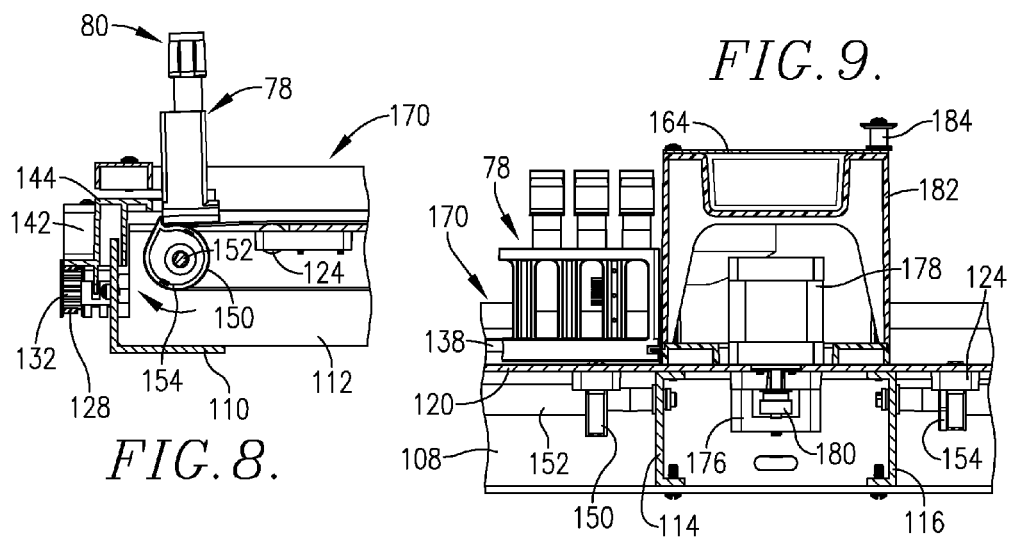
FIG. 8 is a fragmentary vertical sectional view illustrating one of the eccentric pulley lugs engaging a sample rack.
FIG. 9 is a fragmentary central sectional view depicting the drive for the calibrated sample rack.
Figure 10:
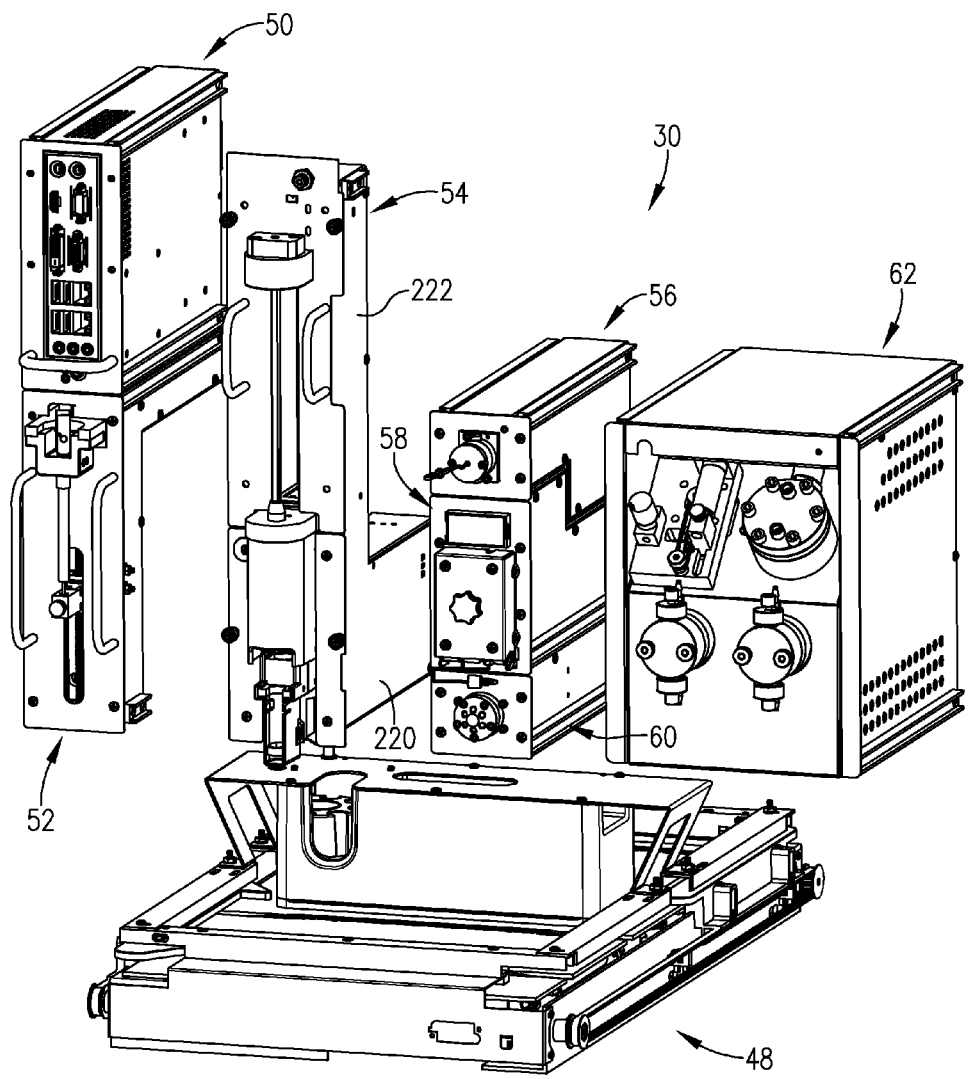
FIG. 10 is an exploded perspective view of the different analyzer modules and their relationship.
Figure 14:
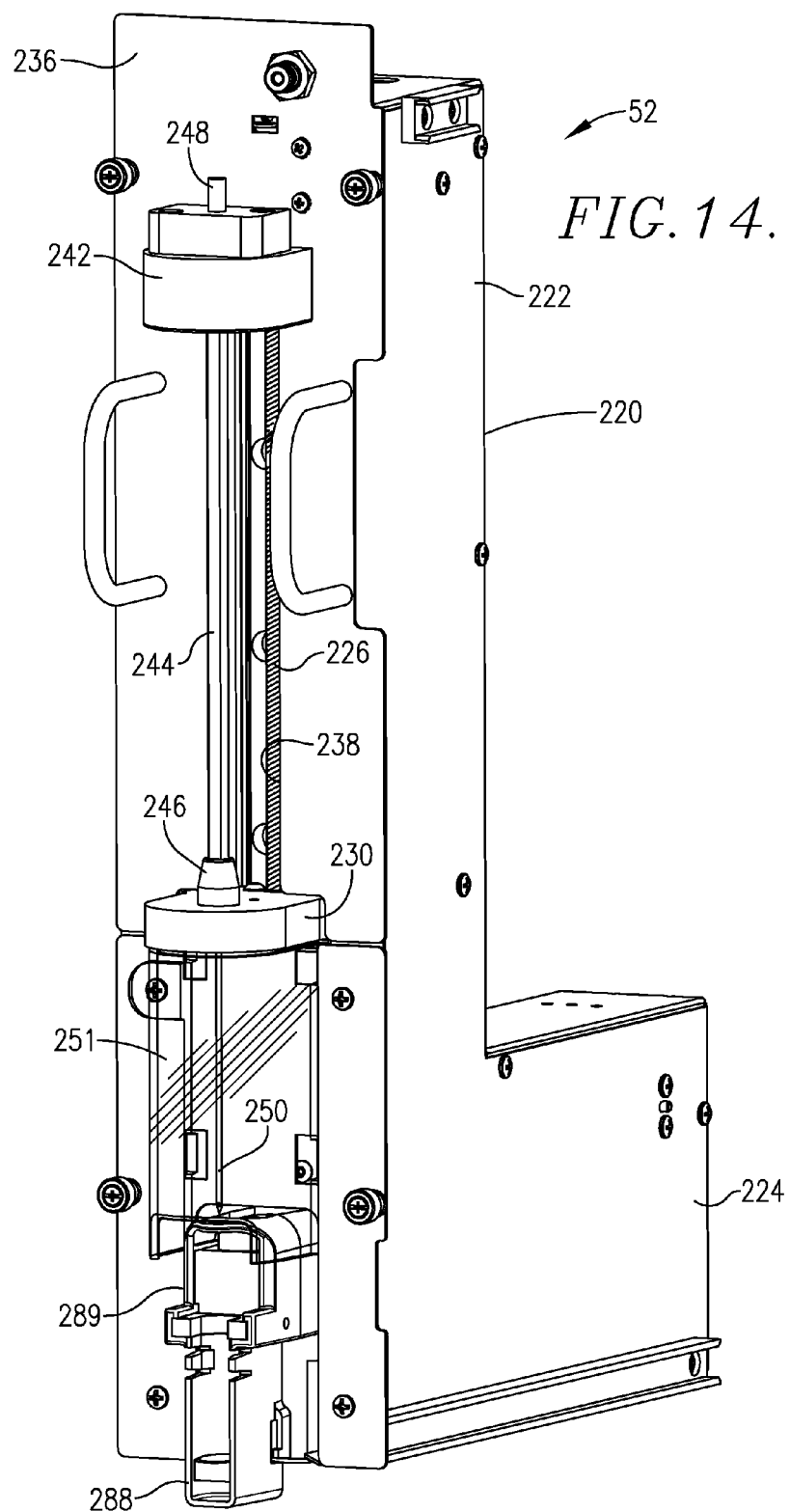
FIG. 14 is a perspective view of the probe module.
Figure 15:
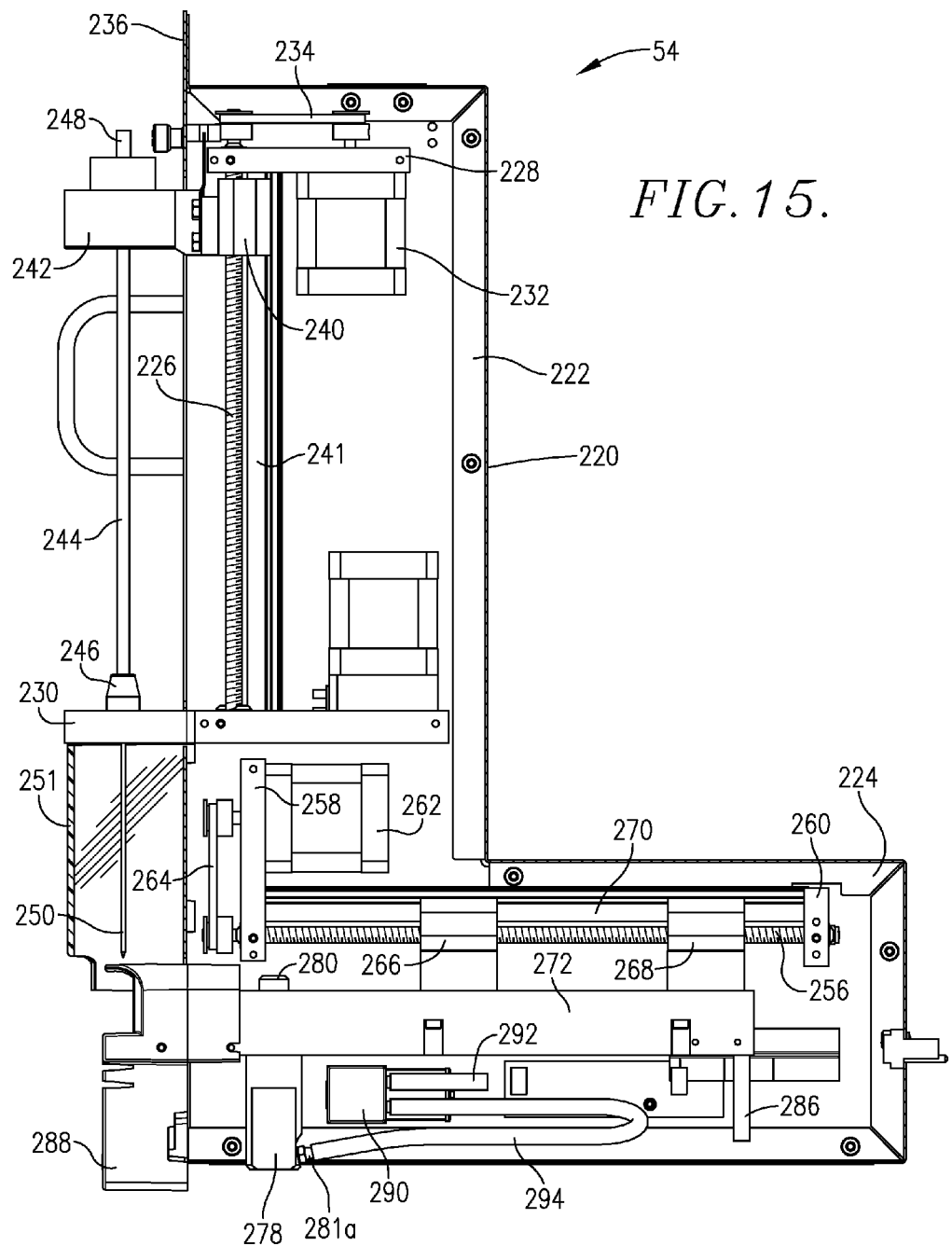
FIG. 15 is a vertical sectional view of the probe module.

The bridge assembly 106 includes an uppermost bridge plate 164 which spans the distance between the side 108, 110 and is equipped with a slot 166 and a test opening 168. The plate 164 is supported by an upper rectangular channel frame 170 by means of oblique legs 171. A rotary calibration rack 172 carrying a plurality of tubes 174 having calibrated samples therein is positioned below the bridge plate 164. The rack 172 is mounted for rotation about an upright axis on a rotary support 176, and is selectively rotated by means of a motor 178 secured to the upper face of base plate 120, and a drive belt 180. The motor 178 is within a housing 182, as best seen in FIG. 9. A latch pin 184 is located on bridge plate 164 and operates in conjunction with a latching assembly (not shown) to releasably secure the rack shifting assembly 97 to cabinet 32.

Motherboard Module 50

This module houses conventional digital processing equipment and has an electronic memory for storing sample analysis programs and data. The motherboard assembly is operably coupled with the other modules and controls the operation thereof. It also is coupled with monitor 46 so as to generate a real-time output of the ongoing sample analyses during operation of the analyzer 30. A keyboard, mouse, and/or other input device is used to load the necessary data within the electronic memory to allow functioning of the module 50.

Syringe Module 52

The syringe module 52 is operably coupled with the probe module 54 described below in order to dilute and collect samples to be analyzed. To this end, the syringe module 52 includes a generally L-shaped housing 186 including a front plate 188 having an elongated slot 190 formed therein. Internally, the module 52 has a vertical drive screw 192 in alignment with the slot 190, and supported by upper and lower stationary blocks 193a, 193b. The screw 192 is driven by means of a motor 194 mounted on upper block 193a and a belt and pulley drive assembly 196.

An external, generally U-shaped fixed block 198 is secured to upper block 193a and has aqueous diluent and output ports 200, 202. The block 198 supports a vertically extending tubular sleeve 204 equipped with an internal plunger rod 206 having an enlarged, liquid-tight head 208. An internally threaded, vertically reciprocal shifter 210 is threaded onto drive screw 192 so as to move the shifter upwardly or downwardly depending upon the direction of rotation of the drive screw. Such movement of the shifter 210 is guided by a stationary guide block 212 mounted to the supports 193a, 193b. The shifter 210 also carries a sensor probe 214 which mates with position sensor 216 within housing 186; this arrangement allows sensing of the vertical position of the shifter 210. The shifter 210 also carries a forwardly extending block 218 which receives the lower end of plunger rod 206, as best seen in FIG. 12. It will be appreciated that vertical movement of the shifter 210 effects corresponding movement of the plunger rod 206.

Probe Module 54

Figure 16:
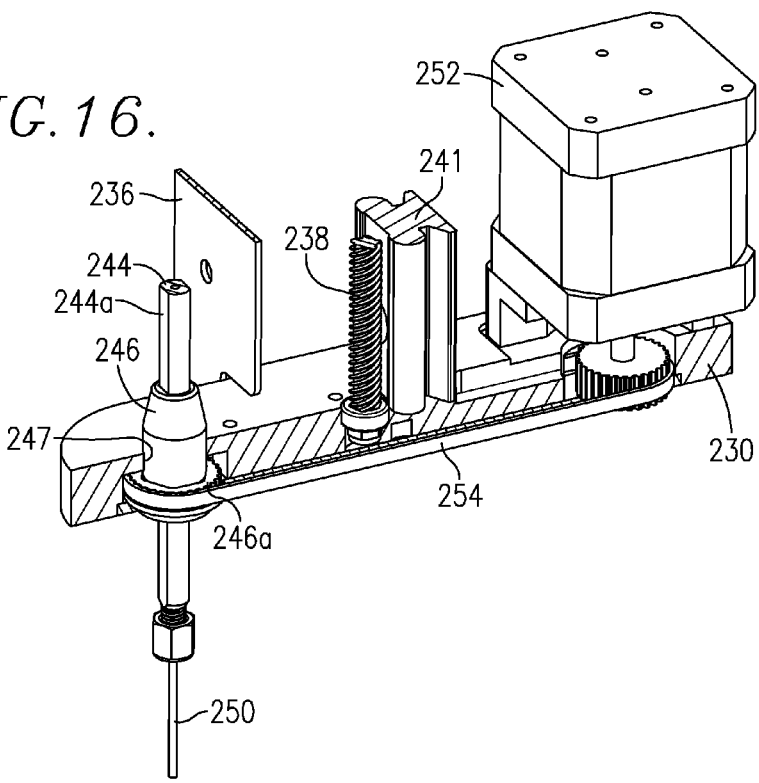
FIG. 16 is a fragmentary perspective view of the rotary drive used to rotate the probe and align each sample tube bar code with the bar code reader.

The probe module 54 is positioned adjacent the syringe module 52 and includes a housing 220 including an upwardly extending section 222 and a rearwardly extending section 224. The section 222 has an internal, vertically extending drive screw 226 supported by upper and lower stationary mounts 228, 230. The screw 226 is rotationally driven by means of a motor 232 secured to mount 228, and a belt and pulley drive assembly 234. The section 222 includes a face plate 236 having an elongated, vertical slot 238 in alignment with drive screw 226. The screw supports a shifter 240 which moves vertically upwardly or downwardly depending upon the direction of rotation of screw 226, and is maintained in alignment by means of a stationary guide 241. The shifter 240 carries an external block 242, which in turn supports an axially rotatable, vertically shiftable needle support 244 having an enlarged spindle 246 received within a bore 247 through the mount 230 (FIG. 16), and an upper connection nipple 248. The fitting 246 includes an enlarged lower section 246a equipped with external teeth.

The needle support 244 has a non-round surface portion which mates with spindle 246, in this instance a pair of opposed flattened surfaces 244a which extend through the spindle 246, so as to permit vertical shifting of the support 244 relative to the spindle, and also to allow rotation of the support 244 via rotation of the spindle 246. The lowermost end of needle support 244 below spindle 246 threadably supports a sharpened sample injection needle 250. The injection needle 250 is protected in its ready position by means of a transparent cover 251. The needle support 244 and injection needle 250 are selectively rotatable by means of a motor 252 supported on mount 230 and a belt drive assembly 254 operably interconnecting the output of motor 252 and the rotational fitting 246.

Figure 17:
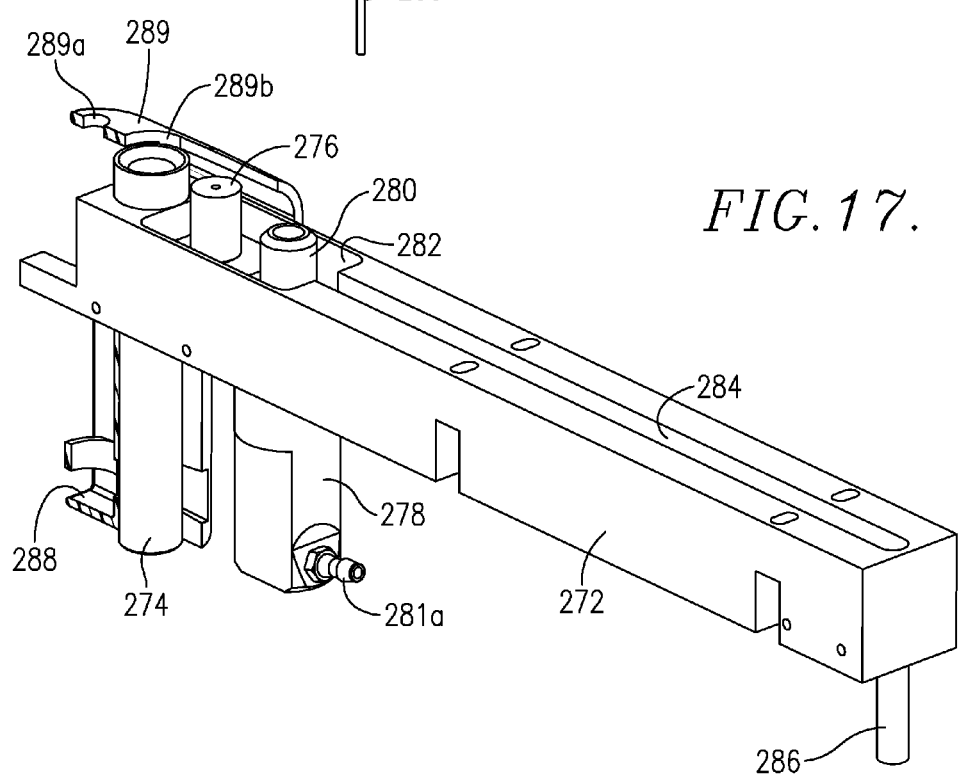
FIG. 17 is a perspective view of the probe module carrier.

The rearwardly extending section 224 of housing 220 has an elongated, horizontally extending drive screw 256 supported by fore-and-aft stationary mounts 258, 260. The screw 256 is selectively rotatable by means of a motor 262 secured to mount 258 and a belt and pulley drive assembly 264. The screw 256 carries a pair of spaced apart shifters 266, 268 which are guided by a stationary rail 270. The shifters 266, 268 support an elongated, fore-and-aft reciprocal carrier block 272 (FIG. 17). The carrier block 272 has a depending, tubular needle guide 274, an injection port 276 including a depending delivery tube 277, and a wash fitting 278 equipped with an upper port 280, a vertical passageway 281, and a wash liquid input nipple 281a. The injection port 276 and port 280 are positioned within a recess 282 formed in carrier block 272, the latter communicating with a drainage slot 284 leading to a waste liquid outlet tube 286.

The carrier block 272 supports a tube holder 288 used to manually test a single sample tube 80, as may be necessary from time to time. The tube holder 288 is secured to the carrier block 272 by means of a hanger component 289 having through apertures 289a, 289b respectively above the holder 288 and the open end of needle guide 274. Additionally, a wash pump 290 is mounted on the sidewall of housing 220 and includes a tubular input 292 and an output 294 operably coupled with nipple 281a.

Figure 19:
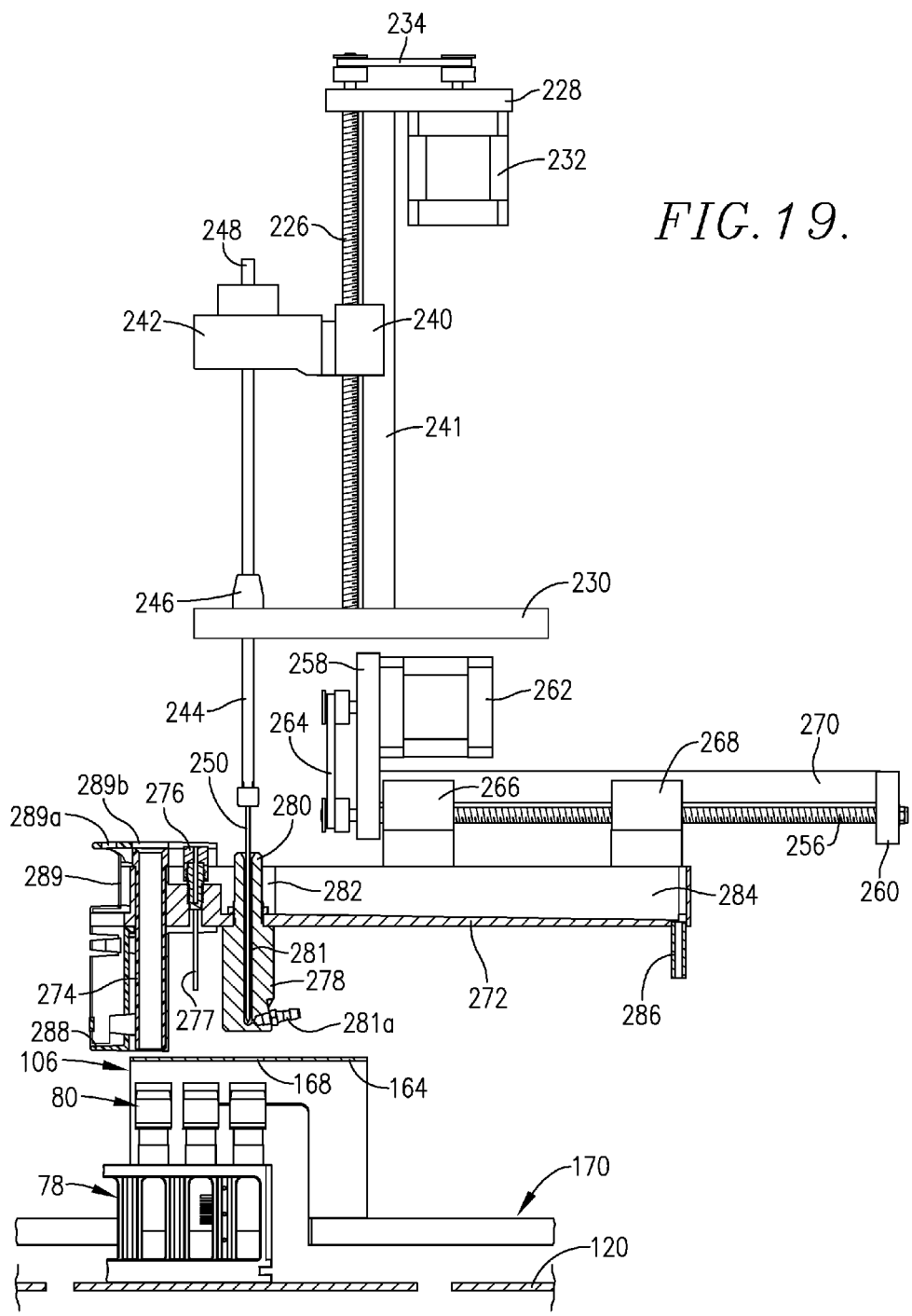
FIG. 19 is a schematic view illustrating the probe module in its sample injection position.
Figure 20:
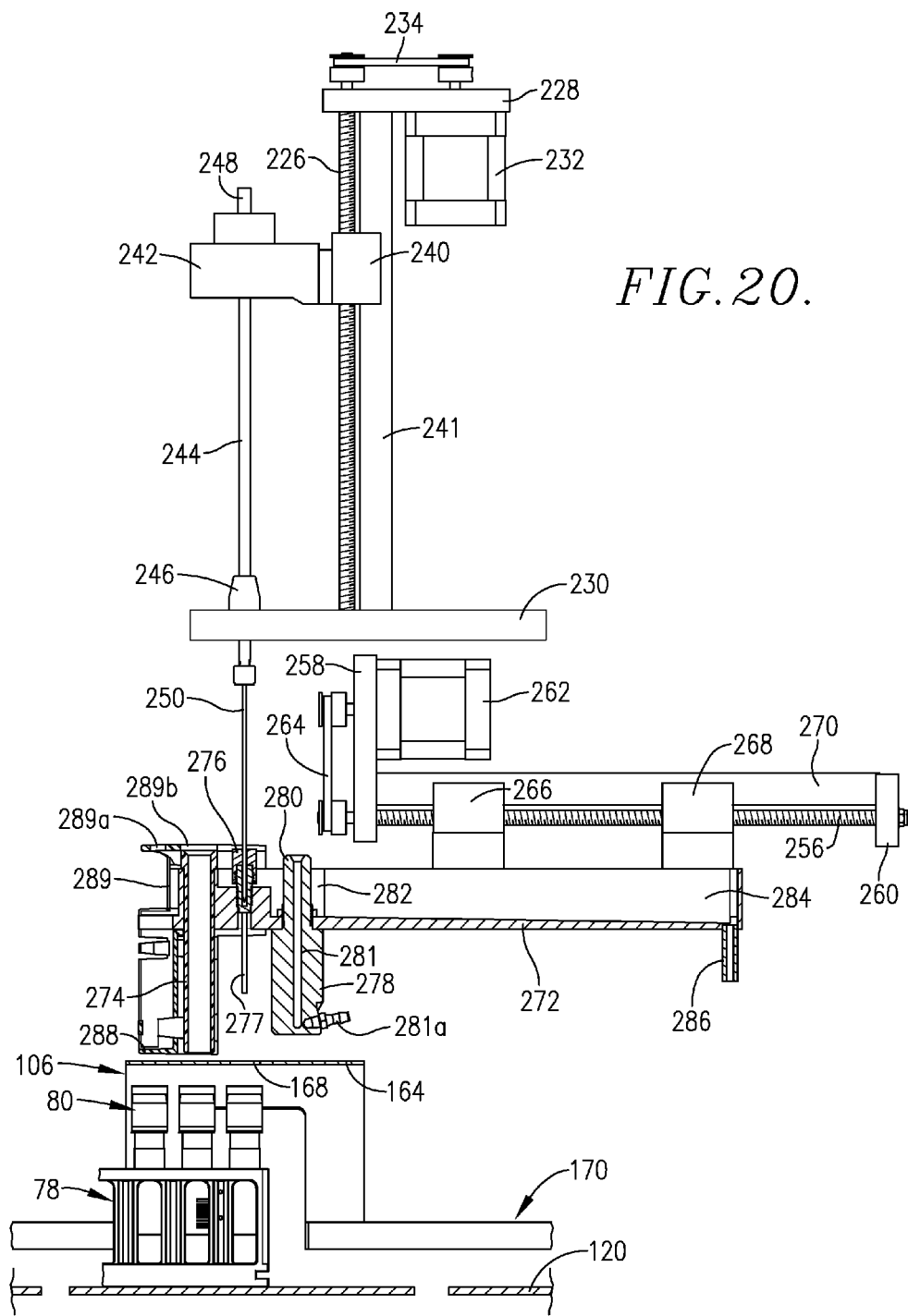
FIG. 20 is a schematic view illustrating the probe module in its needle wash position.

During normal automated operation of analyzer 30 described in detail below, the carrier block 272 is shifted laterally to individual positions, and the needle support 244 carrying needle 250 is correspondingly adjusted vertically. These automated operation positions are depicted in FIGS. 18-20, and are referred to as the diluted sample extraction, diluted sample injection, and needle wash positions.

Figure 18:
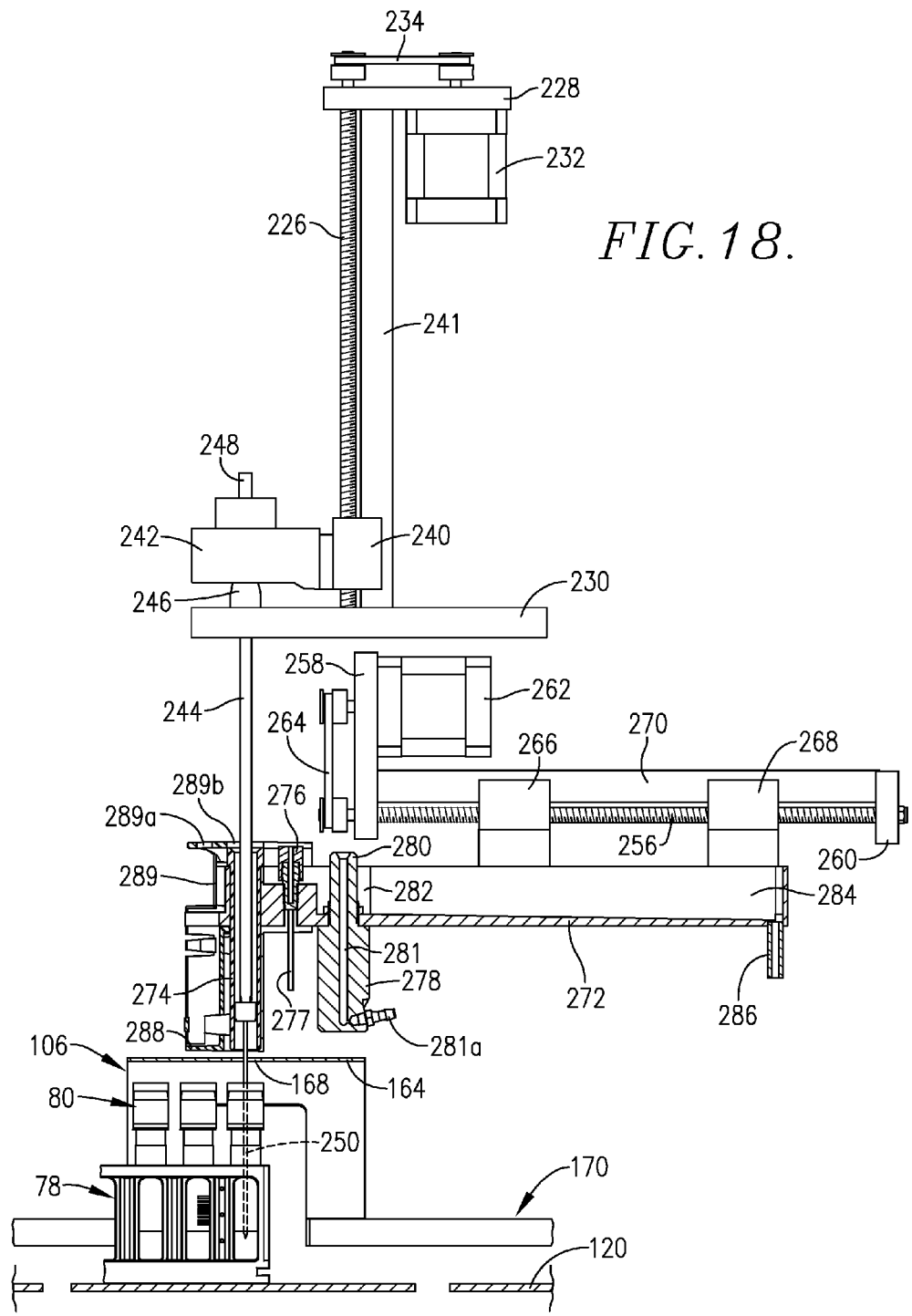
FIG. 18 is a schematic view illustrating the probe module in its sample dilution/extraction position.

Turning first to FIG. 18, it will be observed that the carrier block 272 is shifted laterally to a point where the needle guide 274 is in alignment with injection needle 250. The latter is then shifted downwardly until the needle 250 passes through the test opening 168 and pierces the septum of a sample tube 80. This permits dilution and extraction of a sample from the tube 80. After the needle is fully withdrawn from the guide 274, the carrier block 272 is shifted rightwardly, as viewed in FIG. 20, until the injection port 276 comes into alignment with needle 250. At this point, the needle 250 is lowered into the port 276 and the diluted sample is injected through tube 177. Then (FIG. 20), the needle 250 is moved to the wash fitting 278 and is lowered to allow the needle to be washed for reuse.

In certain instances, it may be desired to test a single sample using the tube holder 288. In such case (FIG. 21), the sample tube 280 is positioned within the holder 288, and the carrier block 272 is positioned so that needle 250 is directly above opening 289a. The needle 250 is then moved downwardly into the holder-mounted tube 80 and a sample is taken. The remaining steps are then identical to those used during automated operation of the analyzer 30.

Injector Module 60

This module is itself entirely conventional, and serves to inject buffering reagents A or B, or mixtures of the reagents A or B and the diluted samples from the injector into the oven module 58, depending upon the stage of operation of the analyzer 30.

Oven Module 58

The oven module 58 (FIGS. 22-25) has a housing 296 having a hingedly mounted front access door 298. Internally, the module 58 includes a heating coil assembly 300 in series with a HPLC column 302, usually an aminophenylboronic acid (PBA) column of known design. The coil assembly 300 includes a shell 304 and an coil 306 forming a part of the line 308 which is wound about an inner spool which also houses a central heating element (not shown). The assembly 300 serves to heat liquid passing through the coil 306, delivering the heated liquid via output line 310 to the HPLC column 302. As the analysis proceeds, the components separated within the column 302 pass through column output 312 for analysis within detector module 56.

Detector Module 56

The detector module 56 is itself conventional and provides spectrophotometric absorbance analyses of the liquid fractions delivered from column 302. The operation and data output from the module 56 are controlled by means of the motherboard module 50, in order to generate an output which can be stored in memory, viewed in real time on monitor 46, or printed in hard copy.

In the case of analyses to qualitatively and/or quantitatively determine levels of glycated and nonglycated proteinaceous fractions within a blood or serum sample, the detector module 56 would typically generate a chromatogram illustrating peaks for nonglycated and glycated proteins at characteristic absorbances, which can be integrated to quantitate the detected species.

Pump Module 62

This module is designed to move all of the liquids involved in operation of analyzer 30 in properly timed, pressurized, and mixed sequences. The module 62 operates in conjunction with a valve assembly 314 and syringe module 52 for these purposes. The valve assembly 314 has input lines 316, 318, 320, 322, respectively from detector module 56, reagent bottle 66, buffer reagent A bottle 68, and buffer reagent B bottle 70. The assembly 314 has reagent A and B output lines 324 and 326, and a waste output line 328.

The module 62 includes pumps 330, 332 for reagents A and B, a syringe prime 334, and a pressure dampener 336. As depicted, the output line 324 from valve assembly 314 is directed to the input of pump A, and the output thereof in line 338 is directed to a tee 340. Similarly, the output line 326 from valve assembly 314 is directed to pump B, and the output from the latter is directed to pressure dampener 336. A return line 341 extends from the output of pump A to wash bottle 72. A separate line 342 extends from the output of pump B to the inlet of pump A. Also, a line 344 extends from wash water bottle 72 to the input of pump B. The output from pressure dampener 336 is conveyed via line 346 to a tee 348, where it may alternately be delivered to syringe prime 334 or to the tee 340. The output from syringe prime 334 passes from line 350 and join with waste line 328.

The pumps A and B are each piston pumps driven by associated cams which rotate 360° during each pump cycle. The cams are powered by stepper motors that divide each 360° cam rotation into 1600 equal steps, with each step corresponding to a fixed amount of rotation of the cam. However, each step does not generate the same positive displacement of the pump piston, meaning that as the cam approaches top dead center, the displacement of the piston approaches zero. In order to overcome this issue, the time between the respective steps is altered so that the displacement of the piston is substantially constant for each step. This linearizes the liquid flow from the pumps during each pump cycle to yield an essentially even flow from each pump during the course of each pump cycle. This operation of the pumps A and B is controlled by the software resident on the motherboard module 50.

Bar Code Assembly 63

The assembly 63 includes a rectangular housing 352 having an observation slot 354 therein. The housing 352 supports a conventional bar code scanner 356 and also has an opening 358 to receive a manual bar code scanner wand 360. The purpose of assembly 63 is to sequentially read the identifying bar codes 86a and 94, respectively, on the racks 78 and the individual sample tubes 80, as the latter pass through the test position of the analyzer 30 and the bar codes come into view through the slot 354.

Operation

1. Initial Conditions

In the ensuing discussion, the continuous operation of analyzer 30 will be described during HPLC spectrophotometric analysis of whole blood samples to qualitatively and quantitatively determine glycated and nonglycated proteinaceous fractions within the samples. The separation column 302 is a standard PBA column used in such analyses. As an initial matter, the column 302 is conventionally equilibrated using reagent B.

Reagent A is designed to enhance the binding of glycated species to the boronate matrix of the column by converting the hydroxylated moieties thereof to the tetrahedryl anionic form. This reagent also serves as a transport medium for the nonglycated proteins initially passing through the column during the analyses. Common reagent A buffers include ammonium salts, phosphates, glycines, morpholine, taurine, and HEPES (N-2-hydroxyethylpiperazine-N-2-ethanesulfonic acid). The ionic strength and pH of reagent A may be adjusted to minimize secondary interactions between the boronate column packing and proteins. Magnesium ions, usually in the form of magnesium chloride ($MgCl2$), may be added to reduce ionic effects without causing hydrophobic bonding. A common reagent A buffer contains, per liter, 250 mmol ammonium acetate, 50 mmol $MgCl2$ at a pH adjusted to between 8.0-9.0. Sodium azide or other preservatives may be employed to enhance shelf life.

Reagent B is designed to elute the glycated components from the column, most frequently by means of a competing polyol which displaces the glycated components from the column binding sites. The preferred reagent B is a mixture of polyol and buffering compound. The most common reagent B consists of, per liter, 100 mmol TRIS (tris(hydroxymethyl)aminomethane), 200 mmol sorbitol, 50 mmol EDTA (ethylenediaminetetraacetic acid), pH 8.0-8.5. Trace amounts of preservatives may also be present.

Venous blood samples, typically collected via venipuncture or finger stick, are mixed with sufficient anticoagulant (e.g., EDTA or heparin) to prevent clotting, and placed within individual tubes 80, which are uniquely identified with a bar code 94, and loaded into racks 78, which are also identified by a separate bar code 86a. The racks 78 are then loaded into a rack shifting assembly 97 to present two banks of side-by-side racks respectively located above the lateral rack transport mechanisms 102 and 104 and between the rack shifters 138 and 144 allowing unimpeded fore-and-aft shifting of the latter (FIG. 4). The loaded assembly 97 is then positioned within tray 96 using the locating pins and apertures 108a, 108b, 110a, 110b, and the latch pin 184.

2. Sequential Rack Shifting

Figure 7:
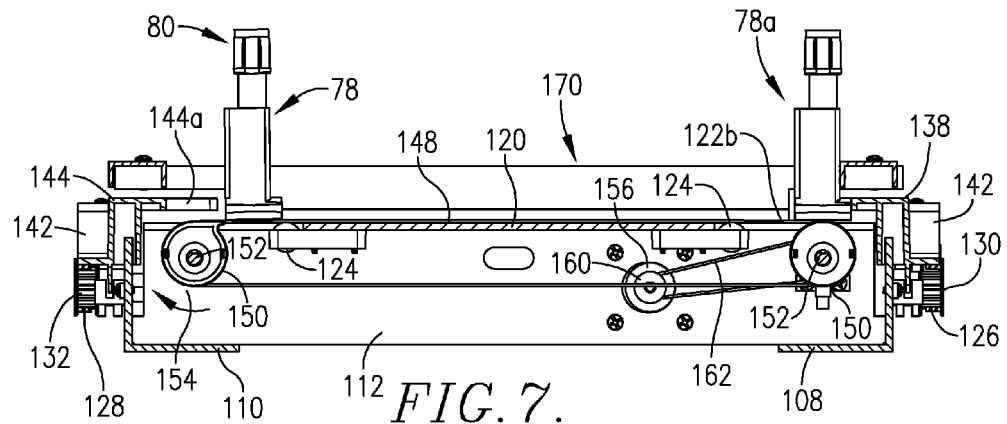
FIG. 7 is a sectional view similar to that of FIG. 6, but showing the belt-supporting eccentric pulleys in the belts-up position to laterally move the racks.

Initially, the mechanisms 102 and 104 are operated in order to shift the racks within the latter, rightwardly in the case of mechanism 102 and leftwardly in the case of mechanism 104 as viewed in FIG. 4, so that the leading loaded racks are moved into the shifters 138 and 144, respectively (e.g., rack 78a). This lateral rack movement is accomplished by energizing the motors 156 and 158a to thereby shift the lateral belts 146 and 148 rightwardly or leftwardly, as the case may be. In addition, during such belt rotation, the lug plates 154 engage the base plates of the adjacent racks 78 to positively shift the abutting racks so that the remote leading racks are fully positioned within the corresponding shifters (FIGS. 7 and 8). Further rotation of the common shafts 152 causes the eccentric pulleys 150 to move to the over-center positions illustrated in FIG. 6, thereby drawing the transverse belts 146, 148 downwardly beneath the axial belts 126 and 128. This in turn permits the racks 78 to be shifted along base plate 120 in a fore-and-aft direction by the belts 126, 128 and the shifters 138 and 144 of the fore-and-aft rack transport mechanism 100, without interference from the belts 146, 148 of the lateral rack transport mechanisms 102 and 104.

In order to move the leading tube 80a of rack 78a into the test station adjacent bar code assembly 63, it is necessary to shift belts 126 and 128 by appropriate activation of the motors 134 and 136 until the leading sample tube 80a of rack 78a comes into alignment with the test opening 168 of bridge 164. The belt 128 is also shifted so as to move shifter 144 as appropriate.\. At this point, the tube 80a is analyzed as described below, and identified by its unique bar code 94. Next, the rack 78a is indexed by additional shifting of belt 126 and shifter 138 until the next succeeding sample tube 80 is aligned with test opening 168, and these steps are repeated. This indexing movement is continued until the last sample tube 80 within the rack 78a is tested. The shifter 144 is also independently moved amount as needed to maintain the sequential movement of the racks 78.

When all of the samples tubes 80 with rack 78a have been analyzed, the rack 78a is now in a position opposite to that illustrated in FIG. 4, i.e., the rack 78a is positioned adjacent the mechanism 104. Also, the loaded and the leading rack within shifter 144 is now positioned adjacent mechanism 102. The mechanisms 102 and 104 are then operated to move the racks from the shifters 138, 144 so as to allow the shifters to be again moved back to the starting positions thereof illustrated in FIG. 4. The mechanisms 102, 104 are again operated to load each of the shifters 138, 144 with a fresh loaded rack 78. This process continues during the course of operation of the analyzer 30 until each sample 80 of each rack 78 passes into the test position above opening 168. Thereupon, rack shifting assembly 97 may be removed from tray 96 (or the original assembly 97 may be reloaded with fresh racks), and the procedure is repeated.

In essence, it will be seen that each rack 78 follows a quadrate path of travel around and through the assembly 97 until the contents of each tube 80 of each rack 78 is analyzed. That is, as depicted in FIG. 4, each rack is conveyed axially rearwardly adjacent the lefthand margin of base plate 120 by belt 128, then laterally (rightwardly) adjacent the rear transverse margin by means of mechanism 102, then axially forwardly adjacent the right-hand margin of base plate 120 by belt 126, and finally laterally (leftwardly) adjacent the front transverse margin by means of mechanism 104.

3. Analysis of Samples

The analysis of samples using an analyzer 30 follows the technique described in U.S. Pat. No. 6,020,203 in terms of the preferred reagents, HPLC column, and processing steps. Accordingly, the disclosure of this patent is incorporated by reference herein in its entirety.

When a sample tube 80 is moved by conveyor module 48 into the test position, a number of steps are followed in order to identify the tube 80, to appropriately mix the contents of the tube 80 with aqueous diluent, to withdraw an aliquot of the diluted sample from the tube 80, to separate the glycated and nonglycated proteinaceous fractions in the sample in HPLC column 302, and to spectrophotometrically analyze the separated species within detector module 56. Those skilled in the art will appreciate that a variety of specific steps may be followed in order to accomplish the analyses; the following discussion represents one preferred procedure.

Specifically, in this procedure, the carrier block 272 is shifted to the FIG. 18 position thereof where needle 250 is in alignment with the guide 274. Thereupon, the needle 250 is shifted downwardly to pierce the septum 92 of the tube 80 to a level permitting withdrawal of the sample aliquot. The frictional engagement between needle 250 and septum 92 allows the sample tube 80 to be rotated by corresponding rotation of the needle support 244 via actuation of motor 252, and in this fashion the tube 80 is rotated until the bar code 94 thereon comes into the view of bar code reader 356. During this sequence, diluent is withdrawn from bottles 74, 76 by operation of syringe module 52 (i.e., the plunger rod 206 is shifted downwardly to draw diluent), which is then injected through needle 250 by upward shifting of the rod 206; appropriate valving with the module 52 permits these operations. Once the sample has been diluted, an aliquot is withdrawn into needle 250, again by operation of syringe module 52.

Next, the needle 250 is fully withdrawn from the sample tube 80. The presence of bridge 164 ensures that there is a clean separation between the needle 250 and the septum 92 of the tube 80, because the upper end of the tube 80 engages the underside of bridge 164 as the needle 250 is withdrawn.

Thereupon, the carrier block 272 is shifted rightwardly, as viewed in FIG. 19, until the injection port 276 is beneath the needle 250. At this point, the latter, containing the diluted and withdrawn aliquot, is injected through the delivery tube 277 to the injector module 60. As this is occurring, reagent A is directed through injector module 60 into and through the column 302 in order to equilibrate and condition the column. The leading reagent A then passes through detector module 56 and is ultimately sent to waste. When the diluted sample enters module 60, it is in-line mixed with the flowing reagent A and ultimately passes through module 58 for separation in column 302. The nonglycated fraction within the sample is thus bound to the PBA matrix within column 302, allowing the glycated fraction to pass therethrough. This glycated fraction is then analyzed in detector module 56 and the effluent is passed to waste. After an appropriate time, passage of reagent A is terminated and reagent B is directed to module 60 for ultimate passage through the column 302 and detector module 56. As reagent B passes through the column, the bound nonglycated proteins are detached from the column and thereupon pass through detector module 56 for quantitation thereof.

After injection, the needle 250 is withdrawn from injection port 276 and the carrier block 272 is moved to the wash position (FIG. 20) where the port is directly beneath the needle. The needle 250 is then moved downwardly within the confines of fitting 278, and wash pump 290 is actuated in order to direct aqueous diluent through nipple 281a and into the interior of fitting 278 to wash the needle for the next analysis. The liquid overflow from fitting 278 passes through drainage slot 284 and outlet tube 286 to waste.

The analyzer 30 is capable of a total analysis time one the order of one minute for each sample within each tube 80, i.e., the injection-to-injection time between individual samples is about one minute, and in preferred forms approximately 66 seconds. These extremely rapid analyses are obtained using the combination of features described above.

During the course of analyses, it may be necessary or helpful to calibrate the analyzer 30 using the rotary calibration rack 172. In this operation, the rack 78 within the testing station is withdrawn by appropriate movement of the rack shifter 138, and the calibration rack 172 is rotated by actuation of the motor 178 until a selected one of the calibrated sample tubes 80 within the rack move into the test position beneath opening 168. At this point, the calibrated sample may be subjected to the same sequence of steps described previously, and the analyzed output is compared with the known characteristics of the calibrated sample; the analyzer 30 may then be adjusted as necessary to calibrate the overall instrument.

Figure 21:
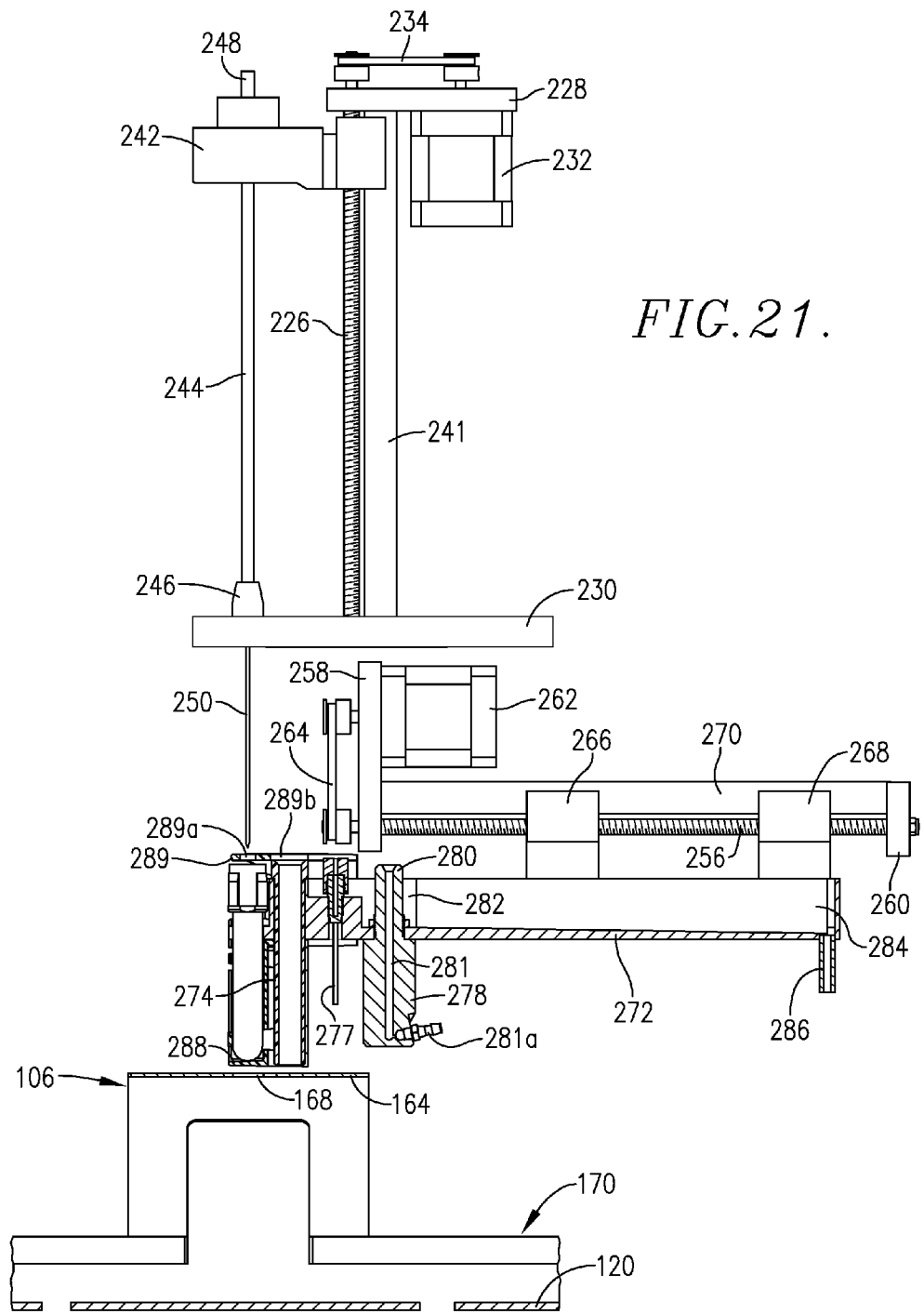
FIG. 21 is a schematic view illustrating the probe module in position to sample a tube in the static holder.
Figure 26:
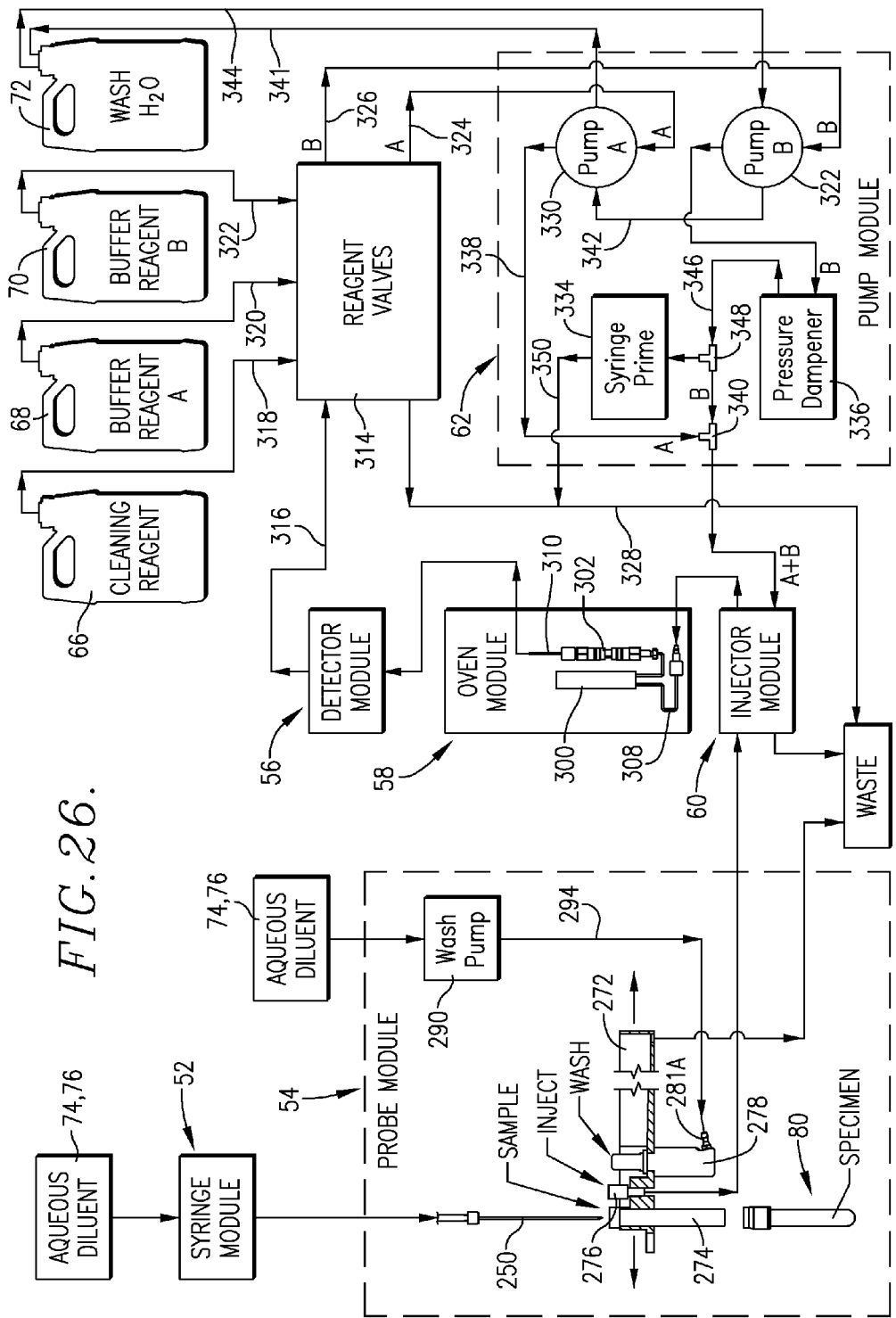
FIG. 26 is a schematic fluid flow block diagram illustrating the operation of the analyzer.

In some instances, it may be helpful or necessary to individually analyze the contents of a given sample tube. As illustrated in FIG. 21, use is made of the stationary tube holder 288. Specifically, a single sample tube is manually placed within the holder 288, and the manual scanner wand 360 is used to scan the bar code associated with the single sample tube. The carrier block 272 is then moved to the FIG. 21 position above opening 289*a* and the sample dilution/withdrawal, injection, and wash steps described previously are followed.

We claim:

1. A sample analyzer comprising an analysis assembly operable to individually analyze a plurality of samples each within a separate container, respective pluralities of said containers located within elongated, shiftable racks, and apparatus operable to shift said racks within the sample analyzer for analysis of each of said samples, said apparatus comprising:
    structure presenting a pair of opposed side margins and a pair of opposed end margins;
    a fore-and-aft shifting assembly operable to individually shift each of said racks in a first direction adjacent one of said side margins, and in the opposite direction along the other of said side margins; and
    a lateral shifting mechanism operable to shift each of said racks in a first lateral direction adjacent one of said end margins, and in the opposite lateral direction adjacent the other of said end margins,
    whereby each of said racks follows a quadrate path of travel,
    said lateral shifting mechanism comprising a first pair of axially spaced apart, laterally extending rack-supporting belts proximal to one of said end margins, and a second pair of axially spaced apart, laterally extending rack-supporting belts proximal to the other of said end margins, said first pair of belts shiftable in one direction, and the other pair of belts shiftable in the opposite direction.

2. The analyzer of claim 1, said fore-and-aft shifting assembly including a pair of elongated, shiftable belts respectively located adjacent said side margins and shiftable in opposite directions, respectively, each of said belts supporting a rack shifter operable to engage and shift a respective rack.

3. The analyzer of claim 1, the belts of said first and second belt pairs each supported on a pair of eccentric pulleys, said pulleys operable to withdraw end sections of said belts in order to prevent interference between the belts and the fore-and-aft shifting of said racks.

4. The analyzer of claim 3, said structure comprising a base plate, said eccentric pulleys located below said base plate, said base plate having slots formed therein adjacent each of said pulleys.

5. The analyzer of claim 1, the belts of said first and second belt pairs each supported on a pair of pulleys, one pulley of each of said sets thereof including a rack-engaging lug operable during rotation of the pulley to engage an adjacent rack to assist in lateral movement thereof.

6. The analyzer of claim 1, said fore-and-aft shifting assembly operable to shift each rack individually and axially, and said lateral shifting mechanism operable to simultaneously shift a plurality of adjacent racks.

7. The analyzer of claim 1, said analysis assembly including a needle operable to extract a portion of each of said samples in order to permit analysis thereof, there being structure operably supporting said analysis needle in order to selectively axially rotate the needle, and to selectively axially shift the needle.

8. The analyzer of claim 1, said container having an external identifying bar code thereon, said sample analyzer including a bar code reader, each of said containers having a septum, said analyzer including a needle operable to pass through said septums, said containers being rotatable in response to rotation of said needle, in order to move said identifying bar codes to a position to be read by said bar code reader.

9. A sample analyzer comprising an analysis assembly operable to individually analyze a plurality of samples each within a separate container, respective pluralities of said containers located within elongated, shiftable racks, and apparatus operable to shift said racks within the sample analyzer for analysis of each of said samples, said apparatus comprising:
    structure presenting a pair of opposed side margins and a pair of opposed end margins;
    a fore-and-aft shifting assembly operable to individually shift each of said racks in a first direction adjacent one of said side margins, and in the opposite direction along the other of said side margins; and
    a lateral shifting mechanism operable to shift each of said racks in a first lateral direction adjacent one of said end margins, and in the opposite lateral direction adjacent the other of said end margins,
    whereby each of said racks follows a quadrate path of travel,
    said analysis assembly including a needle operable to extract a portion of each of said samples in order to permit analysis thereof, there being structure operably supporting said analysis needle in order to selectively axially rotate the needle, and to selectively axially shift the needle.

10. The analyzer of claim 9, said fore-and-aft shifting assembly including a pair of elongated, shiftable belts respectively located adjacent said side margins and shiftable in opposite directions, respectively, each of said belts supporting a rack shifter operable to engage and shift a respective rack.

11. The analyzer of claim 9, said lateral shifting mechanism comprising a first pair of axially spaced apart, laterally extending rack-supporting belts proximal to one of said end margins, and a second pair of axially spaced apart, laterally extending rack-supporting belts proximal to the other of said end margins, said first pair of belts shiftable in one direction, and the other pair of belts shiftable in the opposite direction.

12. The analyzer of claim 11, said structure comprising a base plate, the belts of said first and second belt pairs each supported on a pair of eccentric pulleys, said pulleys operable to withdraw end sections of said belts below said base plate in order to prevent interference between the belts and the fore-and-aft shifting of said racks along said base plate.

13. The analyzer of claim 12, said eccentric pulleys located below said base plate, said base plate having slots formed therein adjacent each of said pulleys.

14. The analyzer of claim 11, the belts of said first and second belt pairs each supported on a pair of pulleys, one pulley of each of said sets thereof including a rack-engaging lug operable during rotation of the pulley to engage an adjacent rack to assist in lateral movement thereof.

15. The analyzer of claim 9, said fore-and-aft shifting assembly operable to shift each rack individually and axially, and said lateral shifting mechanism operable to simultaneously shift a plurality of adjacent racks.

16. A sample analyzer comprising an analysis assembly operable to individually analyze a plurality of samples each within a separate container, respective pluralities of said containers located within elongated, shiftable racks, and apparatus operable to shift said racks within the sample analyzer for analysis of each of said samples, said apparatus comprising:

structure presenting a pair of opposed side margins and a pair of opposed end margins;

a fore-and-aft shifting assembly operable to individually shift each of said racks in a first direction adjacent one of said side margins, and in the opposite direction along the other of said side margins; and a lateral shifting mechanism operable to shift each of said racks in a first lateral direction adjacent one of said end margins, and in the opposite lateral direction adjacent the other of said end margins, whereby each of said racks follows a quadrate path of travel, said container having an external identifying bar code thereon, said sample analyzer including a bar code reader, each of said containers having a septum, said analyzer including a needle operable to pass through said septums, said containers being rotatable in response to rotation of said needle, in order to move said identifying bar codes to a position to be read by said bar code reader.

17. The analyzer of claim 16, said fore-and-aft shifting assembly including a pair of elongated, shiftable belts respectively located adjacent said side margins and shiftable in opposite directions, respectively, each of said belts supporting a rack shifter operable to engage and shift a respective rack.

18. The analyzer of claim 16, said lateral shifting mechanism comprising a first pair of axially spaced apart, laterally extending rack-supporting belts proximal to one of said end margins, and a second pair of axially spaced apart, laterally extending rack-supporting belts proximal to the other of said end margins, said first pair of belts shiftable in one direction, and the other pair of belts shiftable in the opposite direction.

19. The analyzer of claim 18, said structure comprising a base plate, the belts of said first and second belt pairs each supported on a pair of eccentric pulleys, said pulleys operable to withdraw end sections of said belts below said base plate in order to prevent interference between the belts and the fore-and-aft shifting of said racks along said base plate.

20. The analyzer of claim 19, said eccentric pulleys located below said base plate, said base plate having slots formed therein adjacent each of said pulleys.

21. The analyzer of claim 18, the belts of said first and second belt pairs each supported on a pair of pulleys, one pulley of each of said sets thereof including a rack-engaging lug operable during rotation of the pulley to engage an adjacent rack to assist in lateral movement thereof.

22. The analyzer of claim 16, said fore-and-aft shifting assembly operable to shift each rack individually and axially, and said lateral shifting mechanism operable to simultaneously shift a plurality of adjacent racks.

23. The analyzer of claim 16, said analysis assembly including a needle operable to extract a portion of each of said samples in order to permit analysis thereof, there being structure operably supporting said analysis needle in order to selectively axially rotate the needle, and to selectively axially shift the needle.

* * * * *